US011298104B2

(12) United States Patent
Fukuda et al.

(10) Patent No.: US 11,298,104 B2
(45) Date of Patent: Apr. 12, 2022

(54) MEDICAL PROCESSING APPARATUS, ULTRASOUND DIAGNOSTIC APPARATUS, AND MEDICAL PROCESSING METHOD

(71) Applicant: Canon Medical Systems Corporation, Otawara (JP)

(72) Inventors: Shogo Fukuda, Kawasaki (JP); Keita Yonemori, Utsunomiya (JP)

(73) Assignee: Canon Medical Systems Corporation, Otawara (JP)

( * ) Notice: Subject to any disclaimer, the term of this patent is extended or adjusted under 35 U.S.C. 154(b) by 108 days.

(21) Appl. No.: 15/658,624

(22) Filed: Jul. 25, 2017

(65) Prior Publication Data

US 2018/0042573 A1 Feb. 15, 2018

(30) Foreign Application Priority Data

Aug. 10, 2016 (JP) .............................. JP2016-157543
Jul. 20, 2017 (JP) .............................. JP2017-141098

(51) Int. Cl.
*A61B 8/08* (2006.01)
*A61B 8/00* (2006.01)
*G16H 50/30* (2018.01)

(52) U.S. Cl.
CPC ............ *A61B 8/0883* (2013.01); *A61B 8/463* (2013.01); *A61B 8/483* (2013.01); *A61B 8/5223* (2013.01); *G16H 50/30* (2018.01); *A61B 8/488* (2013.01)

(58) Field of Classification Search
CPC ....... A61B 8/0883; A61B 8/463; A61B 8/483; A61B 8/5223; A61B 8/488; A61B 8/461; A61B 8/5212; A61B 8/48
See application file for complete search history.

(56) References Cited

U.S. PATENT DOCUMENTS

| 6,674,879 | B1 * | 1/2004 | Weisman ................. A61B 8/06 378/94 |
| 9,179,892 | B2 * | 11/2015 | Haugen ................ A61B 8/0883 |
| 2004/0254439 | A1 * | 12/2004 | Fowkes .................. G16H 50/20 600/407 |
| 2005/0283078 | A1 * | 12/2005 | Steen ..................... A61B 8/483 600/447 |

(Continued)

FOREIGN PATENT DOCUMENTS

| JP | 2006-006935 | 1/2006 |
| JP | 2009-077961 | 4/2009 |
| JP | 2012-157608 A | 8/2012 |

OTHER PUBLICATIONS

Office Action dated May 18, 2021 in corresponding Japanese Application No. 2017-141098.

*Primary Examiner* — Pascal M Bui Pho
*Assistant Examiner* — Adil Partap S Virk
(74) *Attorney, Agent, or Firm* — Oblon, McClelland, Maier & Neustadt, L.L.P.

(57) ABSTRACT

According to one embodiment, a medical processing apparatus according to an embodiment includes processing circuitry. The processing circuitry acquires a body mark that schematically shows a positional relationship of a plurality of structures in a heart. The processing circuitry analyzes image data as analysis targets which are at least two structures in the heart of a subject, the image data being acquired by scanning the subject. The processing circuitry displays the body mark on a display together with analysis results of the at least two structures.

27 Claims, 15 Drawing Sheets

(56) References Cited

U.S. PATENT DOCUMENTS

| | | | |
|---|---|---|---|
| 2008/0077013 A1* | 3/2008 | Kawagishi | A61B 8/06 |
| | | | 600/443 |
| 2009/0082675 A1 | 3/2009 | Gunji et al. | |
| 2012/0027276 A1* | 2/2012 | Chono | A61B 8/5223 |
| | | | 382/128 |
| 2012/0165674 A1* | 6/2012 | Abe | A61B 8/0883 |
| | | | 600/443 |
| 2015/0190119 A1* | 7/2015 | Park | A61B 8/469 |
| | | | 600/440 |

* cited by examiner

MEDICAL PROCESSING APPARATUS, ULTRASOUND DIAGNOSTIC APPARATUS, AND MEDICAL PROCESSING METHOD

CROSS-REFERENCE TO RELATED APPLICATIONS

This application is based upon and claims the benefit of priority from the prior Japanese Patent Application No. 2016-157543, filed Aug. 10, 2016, and No. 2017-141098, filed Jul. 20, 2017, the entire contents of both of which are incorporated herein by reference.

FIELD

Embodiments described herein relate generally to a medical processing apparatus, an ultrasound diagnostic apparatus, and a medical processing method.

BACKGROUND

In recent years, the demand to perform function analysis on each of a plurality of structures (for example, a left ventricle and a right ventricle) of a heart has increased. However, in a conventional heart function analysis, generally, a single structure of the heart would be focused on, and only an analysis result regarding such structure would be displayed. That is, the usability of when displaying medical information regarding each of the structures of the heart has not been fully considered.

The object is to comprehensively denote the analysis results of the structures of the heart.

DETAILED DESCRIPTION

In general, according to one embodiment, a medical processing apparatus according to the present embodiment includes processing circuitry. The processing circuitry acquires a body mark that schematically shows a positional relationship of a plurality of structures in a heart. The processing circuitry analyzes image data as analysis targets which are at least two structures in the heart of a subject, the image data being acquired by scanning the subject. The processing circuitry displays the body mark on a display together with analysis results of the at least two structures.

An ultrasound diagnostic apparatus according to the present embodiment will be explained with reference to the accompanying drawings. In the description below, structural elements having substantially the same configurations will be denoted by the same reference symbols, and a repetitive description of such elements will be given only where necessary.

Figure 1:
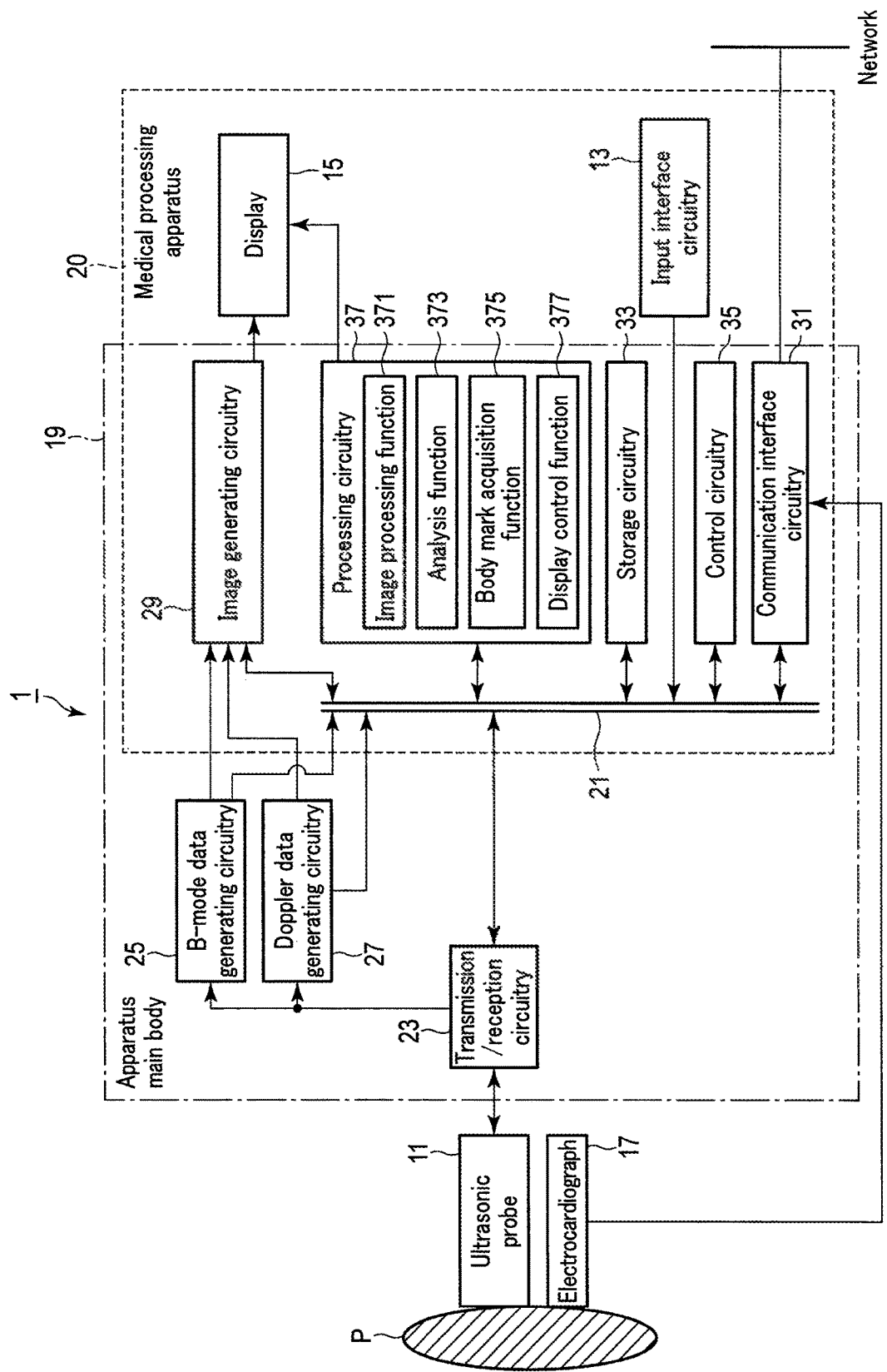
FIG. 1 is a block configuration diagram showing a configuration of an ultrasound diagnostic apparatus according to a present embodiment.

FIG. 1 is a block configuration diagram showing a configuration of an ultrasound diagnostic apparatus 1 according to a present embodiment. As shown in FIG. 1, the ultrasound diagnostic apparatus 1 comprises an ultrasonic probe 11, input interface circuitry (input unit) 13, a display (display unit) 15, an electrocardiograph 17, and an apparatus main body 19.

The ultrasonic probe 11 comprises a plurality of piezoelectric transducers, a matching layer provided on an ultrasonic wave radiation surface side of the piezoelectric transducer, and a backing material provided on a back surface side of the piezoelectric transducer, etc. Each of the plurality of piezoelectric transducers generates ultrasounds in response to a drive signal supplied from transmission/reception circuitry 23 explained later on. The ultrasonic probe 11 is, for example, a two-dimensional array probe in which a plurality of piezoelectric transducers are arrayed along an azimuth direction and an elevation direction that are orthogonal to each other. The two-dimensional array probe is, for example, a two-dimensional sector probe. The ultrasonic probe 11 is not limited to the two-dimensional array probe which is capable of performing three-dimensional scanning, and may also be a mechanical four-dimensional probe. In the case where the ultrasonic probe 11 is a one-dimensional array probe that is capable of performing two-dimensional scanning, a three-dimensional echo signal may be obtained by an operation of an operator swinging the ultrasonic probe 11 in an elevation direction.

An input interface circuitry 13 loads various types of instructions, commands, information, options, and settings from an operator into the present ultrasound diagnostic apparatus 1. The input interface circuitry 13 is realized by a trackball, a switch button, a mouse, a keyboard, a touch pad through which an input operation is carried out by touching an operation surface, and a touch panel display with an integrated display screen and touch pad, etc. The input interface circuitry 13 converts the input operation received from the operator into an electric signal. In the present specification, the input interface circuit 13 is not limited to physical operation members such as a mouse and a keyboard. The input interface circuitry 13 also includes, for example, electric signal processing circuitry that receives an electric signal corresponding to an input operation through an external input device provided separately from the present ultrasound diagnostic apparatus 1, and outputs the received electric signal to the apparatus main body 19.

The display 15 displays various types of images generated by image generating circuitry 29, etc. explained later on. The display 15 comprises display circuitry that realizes display of various types of images. The display 15 displays a Graphics User Interface (GUI) for the operator to input various types of setting requirements. A plurality of displays may be connected to the apparatus main body 19 of the present ultrasound diagnostic apparatus 1.

The electrocardiograph 17 is connected to the apparatus main body 19 through communication interface circuitry 31. The electrocardiograph 17 acquires electrocardiogram (ECG) of a subject P as a biological signal of the subject P subjected to ultrasonic scanning. The electrocardiograph 17 outputs the acquired electrocardiogram to the apparatus main body 19.

The apparatus main body 19 comprises transmission/reception circuitry (transmission/reception unit) 23, B-mode data generating circuitry (B-mode data generating unit) 25, Doppler data generating circuitry (Doppler data generating unit) 27, image generating circuitry (image generating unit) 29, communication interface circuitry 31, storage circuitry (storage unit) 33, control circuitry (controller) 35, and processing circuitry (processing unit) 37.

The transmission/reception circuitry 23 comprises a pulse generator, transmission delay circuitry, and pulser circuitry, and supplies a drive signal to each of a plurality of piezoelectric transducers in the ultrasonic probe 11. The pulse generator repeatedly generates rate pulses for forming transmission ultrasonic waves at a predetermined rate frequency $f_r$Hz (cycle of period; $1/f_r$ second). The transmission delay circuitry gives each rate pulse a delay time necessary to focus transmission ultrasonic waves into a beam and determine transmission directivity. The pulser circuitry applies a voltage pulse to each of the piezoelectric transducers of the ultrasonic probe 11, as a drive signal, at a timing based on the rate pulse. According to this constitution, an ultrasonic beam is transmitted to the subject P.

The transmission/reception circuitry 23 further comprises a preamplifier, an analog to digital (hereinafter, referred to as A/D) converter, reception delay circuitry, and an adder, and generates a reception signal based on a received echo signal generated by each of the piezoelectric transducers. The preamplifier amplifies an echo signal from the subject P received via the ultrasonic probe 11 for each channel. The A/D converter converts the amplified received echo signal into a digital signal. The reception delay circuitry gives the received echo signal that has been converted into a digital signal a delay time necessary for determining reception directivities. The adder adds a plurality of echo signals to which the delay times are given. With this addition processing, the transmission/reception circuitry 23 generates a reception signal in which a reflection component from a direction corresponding to the reception directivity is enhanced. The transmission directivity and the reception directivity determine the comprehensive directivity of ultrasonic transmission/reception. This comprehensive directivity determines an ultrasonic beam (so-called "ultrasonic scanning line").

The B-mode data generating circuitry 25 includes an envelope detector and a logarithmic converter, and generates B-mode data based on the reception signal. The envelope detector executes envelope detection of the reception signal. The logarithmic converter relatively enhances a weak signal in the envelope detected-signal by logarithmically converting the envelope-detected signal. The B-mode data generating circuitry 25 generates a signal value (referred to as B-mode data) for each depth on each scanning line based on the signal enhanced by the logarithmic converter. The B-mode data generating circuitry 25 generates volume data corresponding to three-dimensional B-mode data based on two-dimensional B-mode data obtained by two-dimensional scanning or a reception signal obtained by three-dimensional scanning. For an easy-to-understand explanation, hereinafter, the volume data is assumed as being generated by performing three-dimensional ultrasonic scanning on each of the heart chambers in the subject P. Here, the generated volume data corresponds to each of the structures in the heart. The structures are, for example, a plurality of heart chambers showing four chambers, and a plurality of valves, etc. For an easy-to-understand explanation, hereinafter, the structures will be assumed as being the heart chambers. The four chambers are the left atrium (LA), the left ventricular (LV), the right atrium (RA), and the right ventricular (RV). The volume data may be generated by performing ultrasonic scanning on the four chambers of the heart of the subject P.

The Doppler data generating circuitry 27 includes a mixer and a low pass filter (hereinafter referred to as an LPF) etc., and generates Doppler data based on the reception signal. The mixer multiplies the reception signal by a reference signal having a frequency $f_0$ of a transmission ultrasonic wave to generate a signal having a component with a Doppler shift frequency $f_d$ and a signal having a frequency component of $(2f_0+f_d)$. The LPF removes a signal of a high-frequency component $(2f_0+f_d)$ from signals output from the mixer. In this way, the Doppler data generating circuitry 27 generates Doppler data having the component with a Doppler shift frequency $f_d$ from the reception signal.

The image generating circuitry 29 includes a digital scan converter (hereinafter referred to as DSC) and an image memory, etc. which are both not shown. The DSC converts a scanning line signal string of ultrasonic scanning, which is formed from the B-mode data and the Doppler data, into a video format scanning line signal string (scan conversion). The image generating circuitry 29 generates image data by combining character information of various parameters and a memory, etc. with respect to the scan-converted B-mode data and Doppler data. While the image data is data for display, the B-mode data, the volume data, and the Doppler data are referred to as raw data. The image memory stores a plurality of image data corresponding to a series of frames of a freeze operation immediately before input. A plurality of image data stored in the image memory are used for displaying moving images of the ultrasonic images (cine display).

The communication interface circuitry 31 is connected to an external device such as a medical image storage device through a network. The communication interface circuitry 31 receives the volume data, etc. of the subject P from the medical image storage device, and outputs it to the storage circuitry 33. The communication interface circuitry 31 transfers various types of data output from the image generating circuitry 29 and the processing circuitry 37, etc. to the external device.

The storage circuitry 33 comprises various kinds of memory, an HDD (hard disk drive), an SSD (solid state drive), magnetic disks (such as Floppy (trademark) disks and hard disks), optical disks (such as CD-ROMs and DVDs), and semiconductor memories, etc. The storage circuitry 33 stores a program regarding ultrasonic transmission/reception, and a program corresponding to various types of processing executed by the control circuitry 35 and the processing circuitry 37, etc. The storage circuitry 33 stores raw data, image data, and various types of medical information generated/processed by the processing circuitry 37.

The control circuitry 35 includes, for example, a processor and a memory as a hardware resource. The control circuitry 35 serves as a center of the present ultrasound diagnostic apparatus 1. Specifically, the control circuitry 35 reads a control program stored in the storage circuitry 33 and expands it in the memory, and controls the various types of circuitry of the ultrasound diagnostic apparatus 1 in accordance with the expanded control program.

The processing circuitry 37 includes, for example, a processor and a memory as a hardware resource. Specifically, the processing circuitry 37 reads a program stored in the storage circuitry 33 and expands it in the memory to execute various types of functions in accordance with the expanded program.

The processing circuitry 37 that realizes an image processing function 371 executes an image processing program corresponding to various types of image processing. Specifically, the processing circuitry 37 generates a rendering image by performing rendering processing on the volume data. The rendering image is a three-dimensional image such as a surface rendering image or a volume rendering image. The processing circuitry 37 generates a multi-planar reconstruction (MPR) image as a two-dimensional image by performing MPR processing on the volume data. In the case where the volume data has a plurality of heart chambers, the processing circuitry 37 divides the volume data into volume data of each heart chamber by a predetermined means such as threshold processing. Here, based on the divided volume data, the processing circuitry 37 generates a three-dimensional image for each of the heart chambers. The processing circuitry 37 that realizes the image processing function 371 corresponds to an image processing unit.

The processing circuitry 37 that realizes an analysis function 373 analyzes time series image data (hereinafter referred to as a medical image group) as analysis targets which are at least two structures of the heart of a subject P, the medical image group being acquired by scanning the subject P. Here, the scanning is the ultrasonic scanning mentioned above, and the medical image group is volume data, three-dimensional image data, and two-dimensional image data acquired in a time series. In the case where the present medical processing apparatus 20 is mounted on a computed tomography (CT) apparatus, the above scanning corresponds to an X-ray CT scanning. In the case where the present medical processing apparatus 20 is mounted on a magnetic resonance imaging (MRI) apparatus, the above scanning corresponds to an MR scanning. The processing circuitry 37 acquires the analysis result by analyzing the medical image group. Specifically, the processing circuitry 37 analyzes a wall motion of each heart chamber by applying a predetermined wall motion analysis to the medical image group in each heart chamber. A predetermined wall motion analysis is, for example, a two-dimensional wall motion tracking (WMT) or a three-dimensional WMT; however, is not limited thereto. By executing an analysis program regarding the analysis function 373, the processing circuitry 37 sets, on the image data corresponding to a predetermined heart time phase of the medical image group, a plurality of formation points indicating an outline of a tunica intima of a heart wall, and a plurality of formation points indicating an outline of a tunica externa of the heart wall as initial outlines. The initial outline may be automatically set by predetermined image processing, or may be set by an operator's instruction through the input interface circuitry 13. The initial outline is also appropriately adjustable by the operator's instruction through the input interface circuitry 13. The processing circuitry 37 that realizes the analysis function 373 then tracks positions of the formation points in the other medical data included in the time series medical image group from the image data in which the initial outline is set.

Based on the above tracking result, the processing circuitry 37 that realizes the analysis function 373 calculates a value of various analysis parameters regarding the wall motion of the heart chamber. The analysis parameters are, for example, various types of strains such as a longitudinal strain, or an arrival time of a radial strain of a heart chamber, etc. to a predetermined threshold (hereinafter referred to as peak arrival time), or statistics of various parameters indicating heart functions. The processing circuitry 37 generates a surface rendering image, an MPR image, and a polar map, etc. to which a color phase corresponding to a value of the analysis parameter is mapped, and which are segmented. The segment is a partial area of a heart wall recommended by the American Society of Echocardiography and the American Heart Association. The processing circuitry 37 acquires an image generated by such mapping as a analysis result of the wall motion of each heart chamber. The processing circuitry 37 may also generate, for example, a graph indicating a time change in the value of the analysis parameter in each of a plurality of segments as the analysis result. In the case where the structure of the analysis target is a valve, the analysis result will be an analysis result regarding valve motion. The processing circuitry 37 has the storage circuitry 33 store the generated analysis result. The value of the analysis parameter may be acquired by analytical methods other than the above. The processing circuitry 37 that realizes the analysis function 373 corresponds to an analysis unit.

It should be noted that the expression "processor" used in the above explanation means circuitry, such as, a Central Processing Unit (CPU) or a Graphics Processing Unit (GPU), an Application Specific Integrated Circuit (ASIC), a programmable logic device (for example, Simple Programmable Logic Device (SPLD), a Complex Programmable Logic Device (CPLD), a Field Programmable Gate Array (FPGA)), etc.

The processor realizes various functions by reading and executing a program stored in the storage circuitry 33. Instead of storing various programs on the storage circuitry 33, the various programs may also be directly integrated into the circuitry of the processor in the control circuitry 35 or in the processing circuitry 37. In this case, the processor realizes the various functions by reading and executing the various programs integrated into the circuitry.

The entire configuration of the ultrasound diagnostic apparatus 1 of the present embodiment has been explained above. In the case of realizing the various functions in the present ultrasound diagnostic apparatus by the medical processing apparatus, the medical processing apparatus 20 comprises the components shown inside the dotted frame in FIG. 1. Based on the above configuration, the ultrasound diagnostic apparatus 1 and the medical processing apparatus 20 of the present embodiment are configured to comprehensively display the medical information of the structures of the heart by a body mark acquisition function 375 and a display control function 377 explained below. The medical information includes various types of analysis results generated by the processing circuitry 37, various rendering images generated by the image generating circuitry 29, and an image of a reference cross-sectional surface of the heart, etc. In the following, the display control function 377 will be explained after explaining the body mark acquisition function 375.

The processing circuitry 37 realizing the body mark acquisition function 375 acquires a body mark that schematically shows a positional relationship of a plurality of structures in the heart. When, for example, displaying the medical information (analysis result), this body mark is used in common among different subjects. The structures in the body mark include, for example, models of four chambers defined by the endocardium, and a model of an outer wall of the entire heart. In the case where the medical information includes analysis results regarding each of a plurality of valves (for example, the mitral valve, the tricuspid valve, the aortic valve, and the pulmonary valve), the body mark includes a model corresponding to the valve. Furthermore, in the case where the medical information includes analysis results regarding structures on the outer side of the heart, the structures in the body mark include models corresponding to the structures on the outer side of the heart. The structures on the outer side of the heart are, for example, a coronary artery, a pulmonary artery, a pulmonary vein, a main artery, and a main vein. Instead of the endocardium, the model of the heart chamber in the body mark can be defined by the epicardium, the middle-layer cardiac muscle, the cardiac muscle, or a combination of at least two of the epicardium, the middle-layer cardiac muscle, and the cardiac muscle. The processing circuitry 37 may also acquire a plurality of body marks in a time series. Here, for example, information regarding a heart time phase is added to each of the body marks. The processing circuitry 37 that realizes the body mark acquisition function 375 corresponds to a body mark acquisition unit.

The structures in the body mark may include structures that are not the analysis target. Here, the processing circuitry 37 realizing the body mark acquisition function 375 acquires a body mark in which a display aspect of an area corresponding to the structure of the analysis target is different from a display aspect of an area corresponding to the structure that is not the analysis target. This body mark is, for example, a body mark that highlights an area corresponding to the analysis target. This body mark may be a body mark in which an area that is not the analysis target is made transparent, or a body mark in which the color phase of an area that is not the analysis target is made lighter than the area of the analysis target.

The processing circuitry 37 that realizes the display control function 377 displays the acquired body mark on the display 15 together with the medical information of each of the structures of the heart based on the scanning result of the subject P. The processing circuitry 37 may also have the heart time phase of the medical information and the body mark synchronized, and display the medical information and the body mark on the display 15 as a time series moving image. The processing circuitry 37 that realizes the display control function 377 corresponds to a display control unit.

The structures, for example, include at least two structures. The processing circuitry 37 that realizes the display control function 377 displays the acquired body mark on the display 15 together with the analysis results of at least two structures. Specifically, the processing circuitry 37 displays the analysis results of at least two structures of the heart of the subject P in each of the individual display areas on the display 15. In further detail, the at least two structures include a first structure and a second structure. Specifically, the at least two structures include at least two of the left ventricle, the left atrium, the right ventricle, the right atrium, the mitral valve, the tricuspid valve, the aortic valve, and the pulmonary valve. Here, the body mark includes a first area corresponding to the first structure and a second area corresponding to the second structure. The relative positional relationship between the first area and the second area in the body mark displayed on the display 15 correspond to the arrangement of a first analysis result of the first structure and a second analysis result of the second structure displayed on the display 15.

Figure 2:
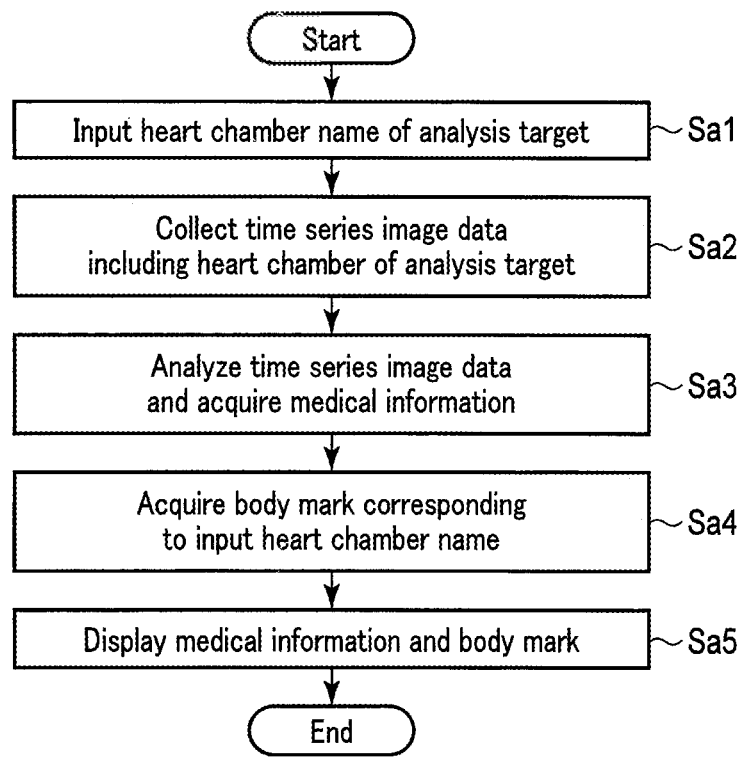
FIG. 2 is a flowchart showing an example of a processing procedure regarding various types of functions in the present embodiment.

The processing regarding the various functions according to the present embodiment will be explained in detail using the flow chart in FIG. 2 in the following. The processing of step Sa3 in FIG. 2 is in regard to the analysis function 373. The processing of step Sa4 in FIG. 2 is in regard to the body mark acquisition function 375. The processing of step Sa5 in FIG. 2 is in regard to the display control function 377.

An operator inputs the name of the structure (for example, the name of a heart chamber or the name of a valve) to be the analysis target through the input interface circuitry 13 (step Sa1). The name of the structure of the analysis target is, for example, utilized for setting an initial outline, or for extracting the initial outline of the heart chamber from the image data, etc. in the analysis function 373. The name of the structure of the analysis target is, for example, used for selecting and processing the body mark in the body mark acquisition function 375. In the case where, in the collected image data, the heart chamber of the analysis target is automatically identified by automatic form recognition, etc., the processing of step Sa1 becomes unnecessary.

The image data including the heart chamber of the analysis target and acquired in a time series is collected by scanning (step Sa2). Specifically, the image data is generated in a time series by transmitting/receiving an ultrasonic wave over a period of one or more heartbeats with respect to each of a plurality of heart chambers. The image data may be read from the storage circuitry 33 or the medical image storage device. In the case of executing a three-dimensional WMT, the image data becomes a three-dimensional image data corresponding to the volume data. In the present embodiment, in some cases, the volume data may indicate a three-dimensional image data obtained as an analysis result by the analysis function 373. In this three-dimensional image data, a color phase corresponding to a value of the analysis parameter is allocated to each voxel corresponding to an analysis portion. At this time, a three-dimensional image of the analysis result is generated by rendering the three-dimensional image data indicating the analysis result. Furthermore, a polar map of the analysis result is generated by applying image processing to the three-dimensional image data indicating the analysis result. Prior to the execution of the analysis function 373, a patient ID, a kind concerning heart chamber, an image mode, and an analysis parameter name, etc. are set. The kind of heart chamber indicates a heart chamber name of an analysis target. The image mode indicates each type of image to which a color phase corresponding to a value of the analysis parameter is mapped, which are, for example, a surface rendering image, an MPR image, and a polar map.

The time series image data is analyzed, and an analysis result is acquired (step Sa3). Specifically, the processing circuitry 37 realizing the analysis function 373 sets a plurality of formation points indicating an initial outline in an image of a predetermined heart time phase, such as an end-diastole, etc. among the obtained time series image data. The processing circuitry 37 then tracks the formation points in the medical image group, and calculates a value of the set analysis parameter. Based on the set image mode and the calculated value of the analysis parameter, the processing circuitry 37 acquires the analysis result of the wall motion of the heart chamber as the medical information.

A body mark corresponding to the input name of the heart chamber is acquired (step Sa4). Specifically, the processing circuitry 37 realizing the body mark acquisition function 375 reads data of the body mark from the storage circuitry 33 or an unillustrated medical image storage device. The data of the body mark is, for example, two-dimensional body mark data. In the case where a body mark depicting a position of one structure in the heart with respect to the entire heart is stored in numbers in the storage circuitry 33 as data of a body mark for each structure, that is, in the case where a plurality of body marks corresponding to a plurality of structures are stored in the storage circuitry 33 as data of a body mark, the processing circuitry 37 selects a body mark corresponding to the name of the heart chamber from the body marks. The data of the body mark corresponds to an anatomical sketch (atlas) of a heart generated without using actual data, and shows the structure of a typical heart. The data of the body mark may be generated in advance by statistical processing with respect to actual data of a heart of each of the subjects, or may be generated by executing this statistical processing by the processing circuitry 37. In this case, the subjects are preferred to be healthy.

The processing circuitry 37 that executes the body mark acquisition function 375 makes the display aspect of the partial area corresponding to the structure of the analysis target (for example, the heart chamber) in the medical information different from the display aspect of the other structures in the data of the body mark. Specifically, the processing circuitry 37 acquires the body mark by emphasizing the area corresponding to the name of the heart chamber in the data of the body mark. In the case where, for example, the medical information includes analysis results regarding the left ventricle, the processing circuitry 37 allocates information regarding highlighting, such as by highlight, color, or hatching, etc. to the left ventricle area in the data of the body mark. In this manner, the processing circuitry 37 acquires a body mark in which the analysis target area is emphasized and displayed. That is, the processing circuitry 37 schematically shows the positional relationship of the structures in the heart, and acquires a body mark in which a display aspect of an area corresponding to at least one structure in the heart is different from the display aspects of areas corresponding to the other structures in the heart. It should be noted that the above highlighting is not essential; therefore, as long as the position of the structure is easy to be visually confirmed by the operator, the display aspect may be of any choice.

The data of the body mark may be data of a three-dimensional body mark (hereinafter referred to as three-dimensional body mark data) which schematically shows a three-dimensional positional relationship of the structures. The three-dimensional body mark data corresponds to volume data schematically showing the structure of a typical heart. Here, the processing circuitry 37 that executes the body mark acquisition function 375, for example, executes the rendering processing with respect to the three-dimensional body mark data under a predetermined rendering condition, and acquires a three-dimensional body mark by the above allocation. That is, the processing circuitry 37 acquires a body mark that schematically shows a positional relationship of a plurality of structures in a heart.

Figure 3:
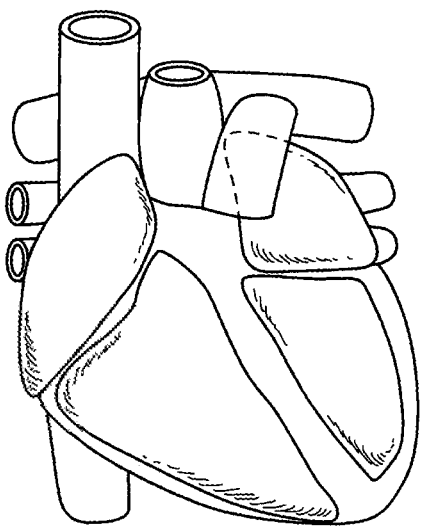
FIG. 3 shows an example of a body mark in the present embodiment.
Figure 4:
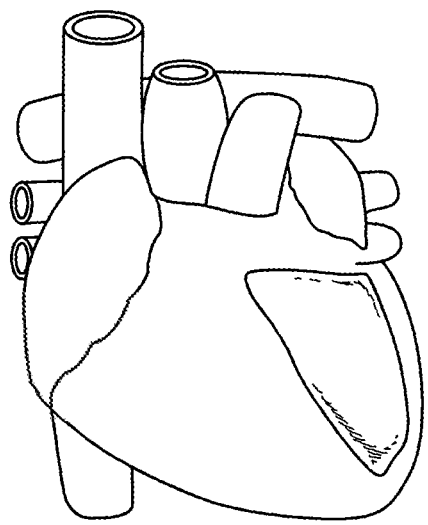
FIG. 4 shows an example of a body mark in the present embodiment.

FIG. 3 and FIG. 4 show an example of a body mark. The body mark in FIG. 3 schematically shows the positional relationship of four chambers with respect to the entire heart when observed from the front. In other words, the body mark in FIG. 3 schematically shows the positional relationship of an outer wall of the heart and four chambers when observed from the front. The body mark in FIG. 4 schematically shows the position of the left ventricle with respect to the entire heart when observed from the front. In other words, the body mark in FIG. 4 schematically shows the positional relationship of an outer wall of the heart and the left ventricle when observed from the front. As shown in FIG. 3 and FIG. 4, the body mark in the present embodiment corresponds to a schematic diagram schematically showing the positional relationship of a plurality of structures with respect to the entire heart.

The processing circuitry 37 that realizes the display control function 377 displays the medical information acquired in step Sa3 and the body mark acquired in step Sa4 on the display 15 (step Sa5). Specifically, the processing circuitry 37 reads a layout for arranging the medical information and the body mark in the display area of the display 15 from the storage circuitry 33. This layout indicates the arrangement of the medical information and the body mark to a plurality of segmented areas in the display area of the display 15. Each of the segmented areas corresponds to the individual display area mentioned above. The processing circuitry 37 then aligns the medical information and the body mark in accordance with the read layout, and displays them on the display 15. In the case where the medical information includes, for example, a plurality of analysis results regarding a single heart chamber, such as the left ventricle, the processing circuitry 37 highlights an area corresponding to the left ventricle in the body mark, and displays it on the display 15 together with the analysis results. In such case, the other structures (the left atrium, the right ventricle, and the right atrium, etc.) in the body mark are not highlighted. The processing circuitry 37 may also have the other structures in the body mark non-displayed.

Figure 5:
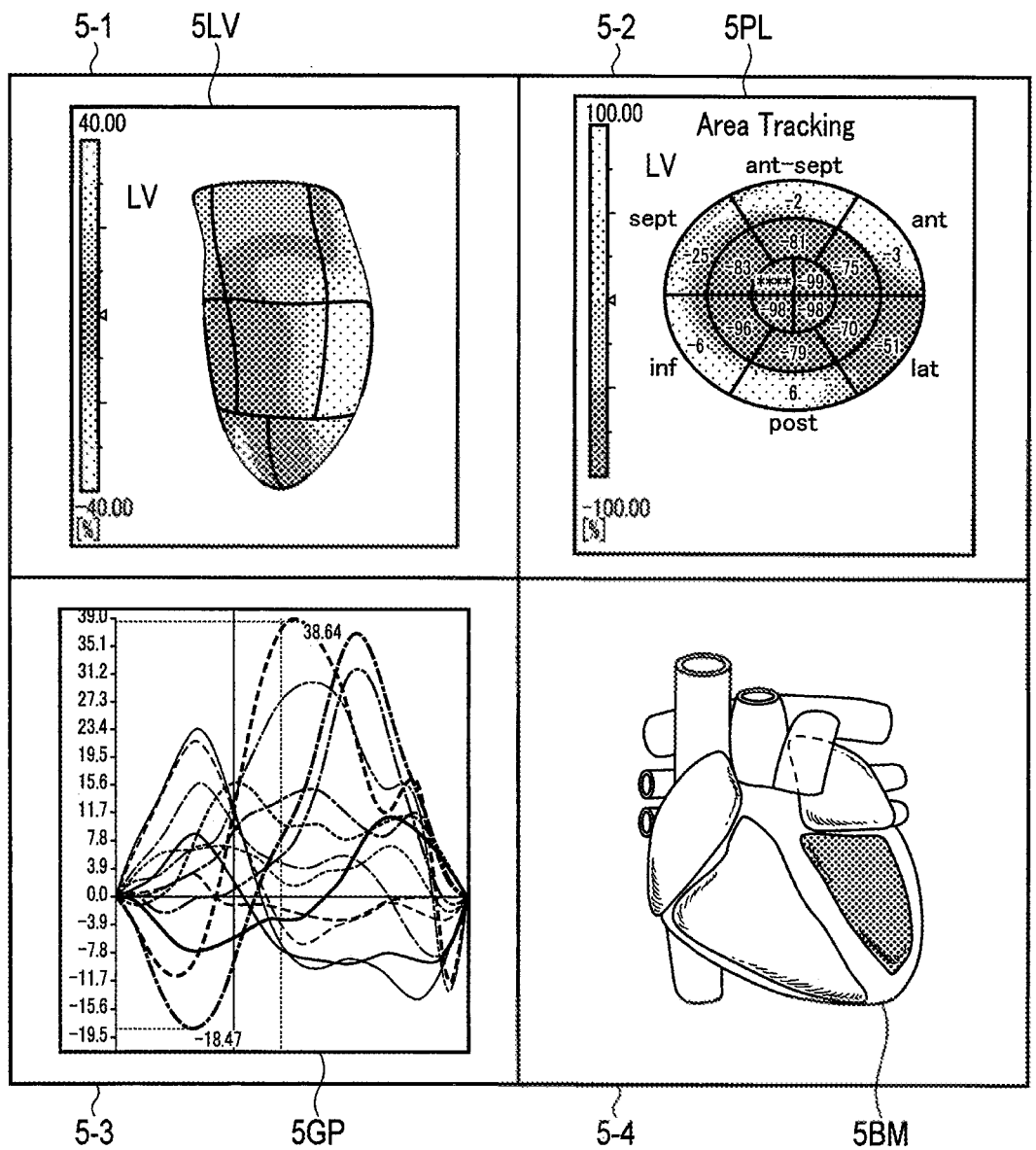
FIG. 5 shows a display example of medical information and the body mark in the present embodiment.

FIG. 5 shows a display example of medical information and a body mark arranged in each of the segmented areas. In segmented area 5-1 shown in FIG. 5, a three-dimensional image (analysis result 5LV) of the left ventricle (LV) to which a color phase corresponding to the value of an analysis parameter is mapped is displayed as a moving image in a state of observing the heart from the front (three-dimensional display). In segmented area 5-2 shown in FIG. 5, a polar map (analysis result 5PL) of the left ventricle (LV), to which a color phase corresponding to the value of an analysis parameter is mapped, is displayed as a moving image (polar map display). In segmented area 5-3 shown in FIG. 5, a graph 5GP that showing a time-change curve of the analysis parameter of the left ventricle (LV) is shown (time-change curve display). In segmented area 5-4 shown in FIG. 5, an acquired body mark 5BM is displayed in a manner of observing the heart from the front. Since all of the medical information in FIG. 5 is the analysis result regarding the left ventricle, an area corresponding to the left ventricle in the body mark 5BM is, for example, highlighted by a hatching pattern.

The three-dimensional display shown in FIG. 5 may be generated by applying rendering processing to three-dimensional image data showing the analysis result, or may be generated by mapping a color phase corresponding to the value of the analysis parameter to a rendering image. The polar map display shown in FIG. 5 may be generated by applying image processing to the three-dimensional image data showing the analysis result, or may be generated by mapping a color phase corresponding to the value of the analysis parameter to a polar map. The analysis result 5LV and analysis result 5PL, which are medical information shown in FIG. 5, are displayed as a moving image in accordance with a heart time phase. Here, the body mark 5BM may be coincided with the heart time phase of the displayed medical information and displayed as a moving image.

According to the configurations mentioned above, the following effects may be obtained.

According to the ultrasound diagnostic apparatus 1 and the medical processing apparatus 20 of the present embodiment, a body mark schematically showing the positional relationship of the structures of the heart can be displayed on the display 15 together with medical information of each of the structures of the heart, based on the scanning result of the subject P. That is, according to the present embodiment, the body mark schematically showing the positional relationship of the structures of the heart can be acquired, the image data can be analyzed as the analysis targets which are at least two structures in the heart of the subject P, the image data being acquired by scanning the subject P, and the body mark can be displayed on a display together with the analysis results of at least two structures. Furthermore, according to the present embodiment, the image data as the analysis targets can be analyzed, the image data being acquired by scanning the subject P. Here, a body mark in which the display aspect of an area corresponding to at least one structure of the heart is different from the display aspect of areas corresponding to the other structures of the heart is acquired, and the acquired body mark can be displayed on the display 15 together with medical information regarding the at least one structure, which is based on the scanning result of the subject P. Furthermore, according to the present embodiment, a plurality of body marks can be acquired in a time series, and the body mark acquired to correspond to a heart time phase of the medical information can be displayed.

Therefore, the present embodiment is capable of displaying the body mark comprehensively showing the medical information (analysis result) of the structures of the heart together with the medical information (analysis result) regarding the structures. This allows an operator to comprehensively grasp the analysis result of the function analysis with respect to the structures. In addition, even in a case where the heart of the subject P is deformed by a disease such as auxocardia, the operator is capable of easily ascertaining the position of the structure regarding the analysis result with respect to the entire heart. Furthermore, by displaying the body mark as a moving image together with a three-dimensional image (rendering image) showing the analysis results in a time series, for example, the schematic shape of the body mark and the rendering image can be compared in each time phase. Therefore, according to the present embodiment, for example, since the heart function analysis can be comprehensively executed, the usability of when simultaneously displaying medical information regarding a plurality of structures of a heart can be improved, which, as a result, would improve diagnostic efficiency.

First Modification

The difference from the above embodiment is that a body mark is acquired in accordance with an orientation (posture) concerning a three-dimensionally displayed analysis result in medical information, and is displayed on the display 15 together with the medical information.

The processing circuitry 37 realizing the image processing function 371 generates a rendering image of volume data that is acquired as an analysis result. A rendering condition used for the rendering image is used when executing the body mark acquisition function 375.

The processing circuitry 37 that executes the body mark acquisition function 375 acquires a body mark in accordance with the rendering condition used for generating the rendering image. Specifically, registration is executed between the volume data and the data of the three-dimensional body mark data. That is, the processing circuitry 37 corresponds the three-dimensional body mark data to the volume data based on the position of the structure in the volume data and the position of the structure in the three-dimensional body mark data. The processing circuitry 37 then acquires the three-dimensional body mark as a body mark by rendering the corresponded three-dimensional body mark data in accordance with the rendering condition. That is, the processing circuitry 37 acquires the body mark (three-dimensional body mark) by rendering the three-dimensional body mark data after the registration in accordance with the condition corresponding to the rendering condition. The processing circuitry 37 may also select a three-dimensional body mark corresponding to the rendering condition from a plurality of three-dimensional body marks stored in advance in the storage circuitry 33. Here, the three-dimensional body marks correspond to a plurality of visual line directions in the rendering condition. The three-dimensional body marks are, for example, two kinds of three-dimensional body marks such as a three-dimensional body mark observed from the front side of the heart and a three-dimensional body mark observed from the back side of the heart.

Figure 6:
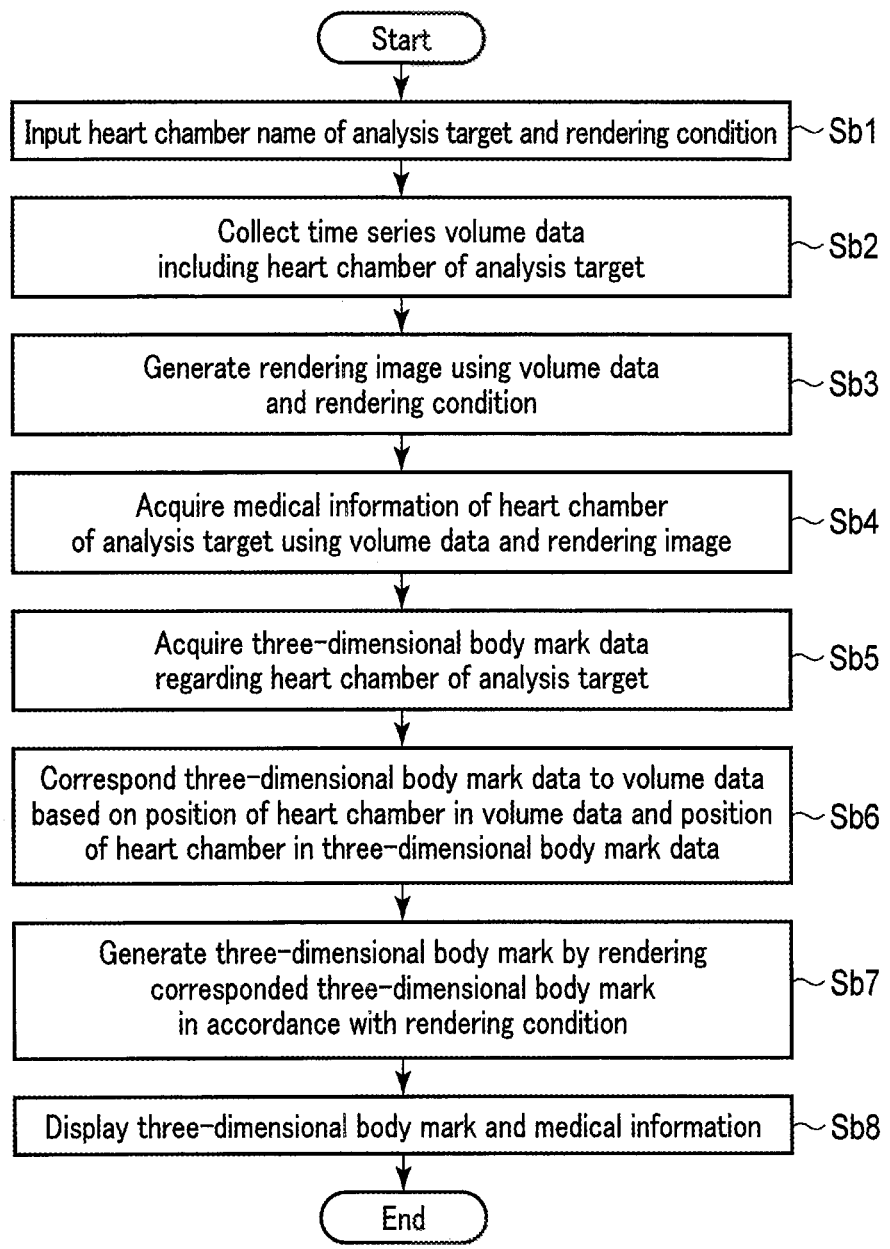
FIG. 6 is a flowchart showing an example of a processing procedure regarding various types of functions in a first modification of the present embodiment.

In the following, the processing regarding the various functions according to the present modification will be explained in detail using the flow chart in FIG. 6. The processing of step Sb3 in FIG. 6 is in regard to the image processing function 371. The processing of step Sb4 in FIG. 6 is in regard to the analysis function 373. The processing of steps Sb5 to Sb7 in FIG. 6 is in regard to the body mark acquisition function 375. The processing of step Sb8 in FIG. 6 is in regard to the display control function 377.

An operator inputs the name of the structure to be the analysis target and the rendering condition (point of view, visual line, etc.) through the input interface circuitry 13 (step Sb1).

The volume data including the heart chamber of the analysis target and acquired in a time series is collected by scanning (step Sb2). Specifically, the volume data obtained in a time series is generated by transmitting/receiving an ultrasonic wave over a period of one or more heartbeats with respect to each of a plurality of heart chambers. The volume data may be read from the storage circuitry 33 or the medical image storage device.

The rendering image is generated by using the volume data and the rendering condition (step Sb3). The rendering image may be generated in response to the change in the visual line direction with respect to the analysis result, such as a rotation operation of the rendering image showing the analysis result.

The medical information of the heart chamber of the analysis target is acquired by using the volume data and the rendering image (step Sb4).

The three-dimensional body mark data regarding the heart chamber of the analysis target is acquired (step Sb5). In the case where a three-dimensional body mark depicting a position of one structure in the heart with respect to the entire heart is stored in plurality in the storage circuitry 33 as three-dimensional body mark data for each structure, the processing circuitry 37 selects a three-dimensional body mark corresponding to the name of the heart chamber from the three-dimensional body marks. Subsequent to the processing of step Sb5, information regarding highlighting is mapped to an area corresponding to the name of the heart chamber in the acquired three-dimensional body mark. The information regarding highlighting may also be mapped to the area of the target heart chamber in the three-dimensional body mark after the rendering processing mentioned later on.

The three-dimensional body mark data is corresponded to the volume data based on the position of the heart chamber in the volume data and the position of the heart chamber in the three-dimensional body mark data (step Sb6). Specifically, the processing circuitry 37 that executes the body mark acquisition function 375 reads the three-dimensional body mark data including the heart chamber of the analysis target (hereinafter referred to as the target heart chamber) from the storage circuitry 33. The processing circuitry 37 then corresponds the target heart chamber in the three-dimensional body mark data to the target heart chamber in the volume data. The above correspondence, for example, is equivalent to execute registration between the target heart chamber in the three-dimensional body mark data and the target heart chamber in the volume data. Specifically, the correspondence performed by the processing circuitry 37, for example, corresponds a plurality of coordinates indicating the area of the target heart chamber in the three-dimensional body mark data to a plurality of coordinates indicating the area of the target heart chamber in the volume data. In this manner, the orientation of the target heart chamber in the three-dimensional body mark data is corresponded to the orientation of the target heart chamber in the volume data.

Figure 7:
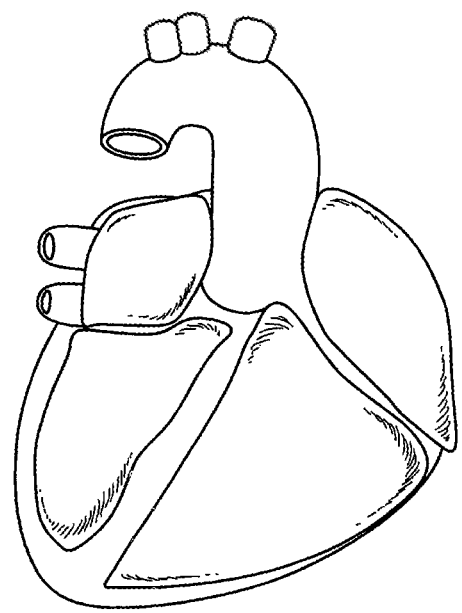
FIG. 7 shows an example of a body mark in the first modification of the present embodiment.

The three-dimensional body mark is generated by rendering the three-dimensional body mark data after the registration in accordance with the rendering condition (step Sb7). By the above rendering processing, the processing circuitry 37 that realizes the body mark acquisition function 375 acquires the three-dimensional body mark as a body mark. In the case where, for example, an analysis result obtained by mapping a color phase corresponding to the value of an analysis parameter to a three-dimensional image of the left ventricle is displayed as a moving image in a state of being observed from the back side, the point of view in the rendering condition would be set to the back side of the heart. FIG. 7 shows an example of a body mark in the case where the point of view is set to the back side of the heart.

In other words, the body mark in FIG. 7 schematically shows the positional relationship of an outer wall of the heart and four chambers observed from the back. The difference between FIG. 7 and FIG. 3 is that the orientation (posture) of the body mark is different between the front side and the back side of the subject P. Instead of the processing in step Sb7, the three-dimensional body mark corresponding to the rendering condition may also be selected from the three-dimensional body marks stored in advance in the storage circuitry 33.

Figure 8:
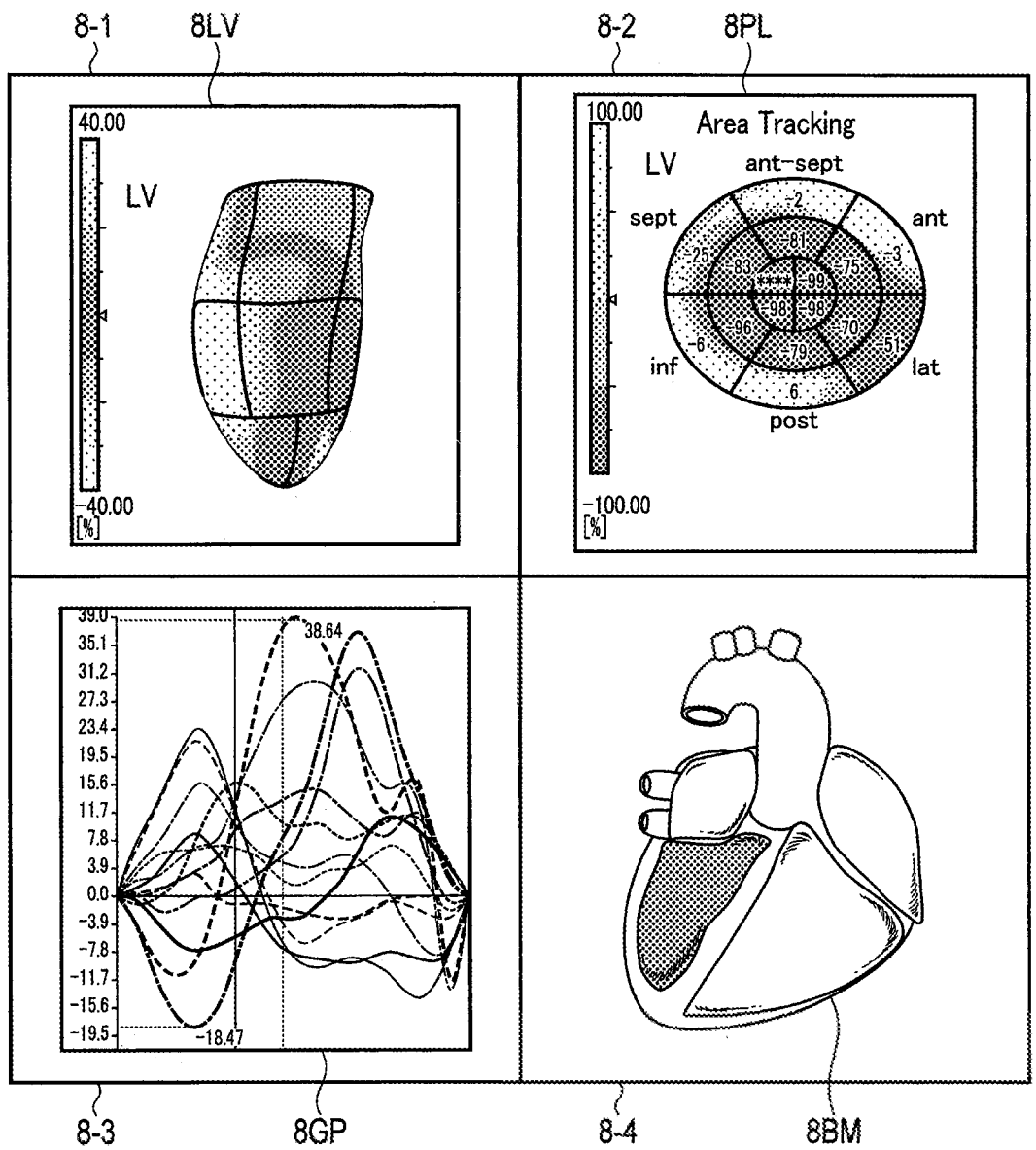
FIG. 8 shows a display example of medical information and the body mark in the first modification of the present embodiment.

The three-dimensional body mark and the medical information are displayed on the display 15 (step Sb8). FIG. 8 shows a display example of the medical information and the body mark arranged in each of a plurality of segmented areas. In segmented area 8-1 shown in FIG. 8, a three-dimensional image (analysis result 8LV) of the left ventricle (LV), to which a color phase corresponding to the value of an analysis parameter is mapped, is displayed as a moving image in a state of observing the subject P from the back (three-dimensional display). In segmented area 8-2 shown in FIG. 8, analysis result 8PL corresponding to the analysis result 5PL in FIG. 5 is displayed as a moving image (polar map display). In segmented area 8-3 shown in FIG. 8, graph 8GP corresponding to the graph 5GP in FIG. 5 is displayed (time-change curve display). In segmented area 8-4 shown in FIG. 8, an acquired body mark 8BM is oriented in the same manner as the three-dimensional image in the analysis result 8LV, and is displayed. That is, since the analysis result 8LV in FIG. 8 is in a state where the subject P is observed from the back, as shown in FIG. 8, the body mark 8BM schematically shows the positional relationship of four chambers with respect to the entire heart observed from the back. Since all of the medical information in the display example of FIG. 8 is the analysis result regarding the left ventricle, an area corresponding to the left ventricle in the body mark 8BM is, for example, highlighted by a hatching pattern.

The input of the rotation operation with respect to the analysis result 8LV shown in FIG. 8 corresponds to changing the visual line direction and the point of view in the rendering condition. Therefore, triggered by the input of the rotation operation with respect to the analysis result 8LV, each processing in step Sb3, step Sb4, step Sb7, and step Sb8 is repeated. The three-dimensional body mark is also rotated and displayed in accordance with the rotation of the analysis result in the three-dimensional display. That is, the body mark 8BM is rotated and displayed cooperatively with the orientation of the three-dimensional image in the medical information.

According to the configurations mentioned above, the following effects may be obtained.

According to the ultrasound diagnostic apparatus 1 and the medical processing apparatus 20 in the present modification, a rendering image is generated by applying rendering processing to volume data acquired as an analysis result, and a body mark can be acquired in accordance with the rendering condition in this rendering processing. Specifically, the body mark can be acquired by executing registration between the volume data acquired as the analysis result and the three-dimensional body mark data, and rendering the three-dimensional body mark data after the registration in accordance with a condition corresponding to this rendering condition. In this manner, the orientation (posture) of the three-dimensionally displayed analysis result and the orientation (posture) of the body mark can be corresponded and displayed.

Therefore, according to the present modification, an operator is capable of comprehensively and intuitively ascertaining the analysis result of the function analysis with respect to the structure, in accordance with the visual line direction in the three-dimensional display. Therefore, according to the present modification, since the heart function analysis can be comprehensively executed, the usability of when simultaneously displaying medical information regarding a plurality of structures of a heart can be improved, which, as a result, would improve diagnostic efficiency.

Second Modification

The difference from the above embodiment is that each of a plurality of body marks, in which each of a plurality of structures is emphasized, is displayed together with three-dimensionally displayed medical information of each of the structures.

The processing circuitry 37 realizing the body mark acquisition function 375 acquires the body marks in which each of the structures is emphasized based on body mark data and medical information. Specifically, the processing circuitry 37 reads the body mark data including the structures from the storage circuitry 33. The processing circuitry 37 generates a plurality of body marks in which each of the structures is presented in different display aspects, based on the read body mark data and the medical information. The different display aspects are, for example, highlighting, which emphasizes the structures in the body mark in accordance with the medical information.

The processing circuitry 37 that realizes the display control function 377 displays the acquired body mark on the display 15 together with the medical information of each of the structures, which is based on the scanning result of the subject P.

Figure 9:
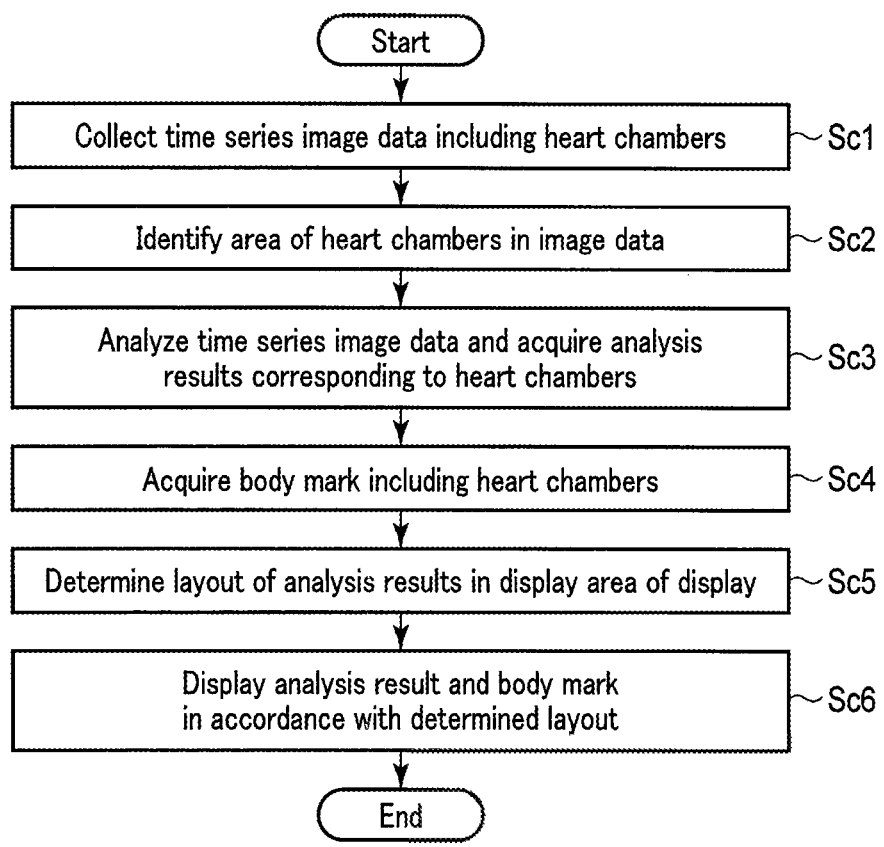
FIG. 9 is a flowchart showing an example of a processing procedure regarding various types of functions in a second modification of the present embodiment.

In the following, the processing regarding the various functions according to the present modification will be explained in detail using the flow chart in FIG. 9. The processing of steps Sc2 and Sc3 in FIG. 9 is in regard to the analysis function 373. The processing of step Sc4 in FIG. 9 is in regard to the body mark acquisition function 375. The processing of steps Sc5 to Sc6 in FIG. 9 is in regard to the display control function 377.

By scanning the heart of the subject P, image data obtained in a time series that includes a plurality of heart chambers is collected at one time (step Sc1).

Subsequently, an area of each of the heart chambers is designated with respect to the image data through the input interface circuitry 13. In the above manner, areas of the heart chambers in the image data are identified (step Sc2). In the case where the heart chambers in the collected image data are automatically identified by automatic form recognition, etc., it would become unnecessary to designate the area of each of the heart chambers through the input interface circuitry 13.

By analyzing the image data obtained in a time series, each of a plurality of analysis results corresponding to the heart chambers is acquired as medical information (step Sc3). The structures are, for example, a first structure and a second structure. The processing circuitry 37 that realizes the analysis function 373, for example, analyzes the image data as an analysis target which is the first structure of the heart of the subject P, the image data being acquired by scanning the subject P. The processing circuitry 37 also analyzes the image data as an analysis target which is the second structure of the heart of the subject P, the image data being acquired by scanning the subject P. Here, the acquired medical information is first medical information regarding the first structure (a first analysis result, etc.) and second medical information regarding the second structure (a second analysis result, etc.). The first medical information and the second medical information include three-dimensionally displayed analysis results. Step Sc2 and step Sc3 may be repeated for each structure of analysis targets, such as for each heart chamber. In the case of collecting image data for each structure in step Sc1, the processing of step Sc1 to Sc3 is repeated for each structure.

A body mark including the heart chambers is acquired (step Sc4). The processing circuitry 37 that realizes the body mark acquisition function 375, for example, acquires a first body mark. The first body mark schematically shows the positional relationship of the first structure and the second structure of the heart. In the first body mark, a display aspect of an area corresponding to the first structure is different from the display aspect of an area corresponding to the second structure. The processing circuitry 37 acquires a second body mark. The second body mark schematically shows the positional relationship of the first structure and the second structure of the heart. In the second body mark, the display aspect of the area corresponding to the first structure is different from the display aspect of the area corresponding to the second structure. In accordance with the choice of medical information regarding the first structure of the heart displayed on the display 15, the processing circuitry 37 may acquire a body mark in which the display aspect of an area corresponding to the first structure is different from the display aspect of an area corresponding to the second structure of the heart. Specifically, the processing circuitry 37 realizing the body mark acquisition function 375 generates a plurality of body marks in which the structure in the medical information is highlighted. Each of the body marks has a display aspect in which each of the areas corresponding to the structure in the medical information is highlighted. The processing circuitry 37 corresponds the orientation of the body mark to the orientation of the three-dimensionally displayed medical information. The processing circuitry 37 may also acquire one body mark that is capable of displaying areas of a plurality of structures. Here, the body mark includes, for example, a first area corresponding to the first structure and a second area corresponding to the second structure.

The layout of the analysis results in the display area of the display is determined based on each kind of structure (heart chamber name, valve name) in the medical information (step Sc5). The layout of the analysis results corresponds to, for example, a form that shows which analysis result is to be arranged in which position of the display area at which size. Specifically, the processing circuitry 37 that realizes the display control function 377 determines the layout based on an analysis parameter in the medical information, each kind of structure (or anatomical positional relationship of the structure), a phase of a stress echo, and treatment progress, etc. In the case of, for example, displaying medical information concerning each of the four chambers in a display area of the display 15, a layout would be obtained in which an analysis result of the right atrium is arranged in a segmented area on the upper left of the display area, an analysis result of the right ventricle is arranged in a segmented area on the lower left of the display area, an analysis result of the left atrium is arranged in a segmented area on the upper right of the display area, and an analysis result of the left ventricle is arranged in a segmented area on the lower right of the display area. In the case of, for example, displaying medical information concerning a stress echo with respect to the right ventricle and the left ventricle in a display area of the display 15, a layout would be obtained in which an analysis result regarding the right ventricle at rest is arranged in a segmented area on the upper left of the display area, an analysis result regarding the right ventricle under stress is arranged in a segmented area on the lower left of the display area, an analysis result regarding the left ventricle at rest is arranged in a segmented area on the upper right of the display area, and an analysis result regarding the left ventricle under stress is arranged in a segmented area on the lower right of the display area. The above explanation of the layout is an example, and would not be limited thereto.

The analysis result and the body mark are displayed in accordance with the determined layout (step Sc6). The processing circuitry 37 that realizes the display control function 377 displays the first body mark on the display 15 together with the analysis results of the first structure. Specifically, the processing circuitry 37 displays the first body mark in the display area of the first medical information regarding the first structure, and displays the second body mark in the display area of the second medical information regarding the second structure. In the case where the body mark includes the first area corresponding to the first structure and the second area corresponding to the second structure, the processing circuitry 37 displays this body mark on the display 15 together with the first medical information regarding the first structure and the second medical information regarding the second structure. Here, the relative positional relationship between the first area and the second area in the body mark displayed on the display 15 corresponds to an alignment (arrangement) of the first medical information and the second medical information displayed on the display 15. Specifically, the processing circuitry 37 realizing the display control function 377 further displays the body mark in a display area (segmented area) of the medical information in the display area of the display 15, and emphasizes and displays an area of the structure regarding the medical information in the body mark. When the medical information displayed on the display 15 is selected by the operator, the processing circuitry 37 emphasizes and displays the area of the structure regarding the selected medical information in the body mark. In accordance with, for example, the choice of medical information regarding the first structure of the heart displayed on the display 15, the processing circuitry displays on the display 15 a body mark in which the display aspect of an area corresponding to the first structure is different from the display aspect of an area corresponding to the second structure of the heart. The processing circuitry 37 may determine a display position of the body mark corresponding to the medical information based on a rendering direction in the rendering conditions. In the following, various display examples in the present modification will be explained.

Figure 10:
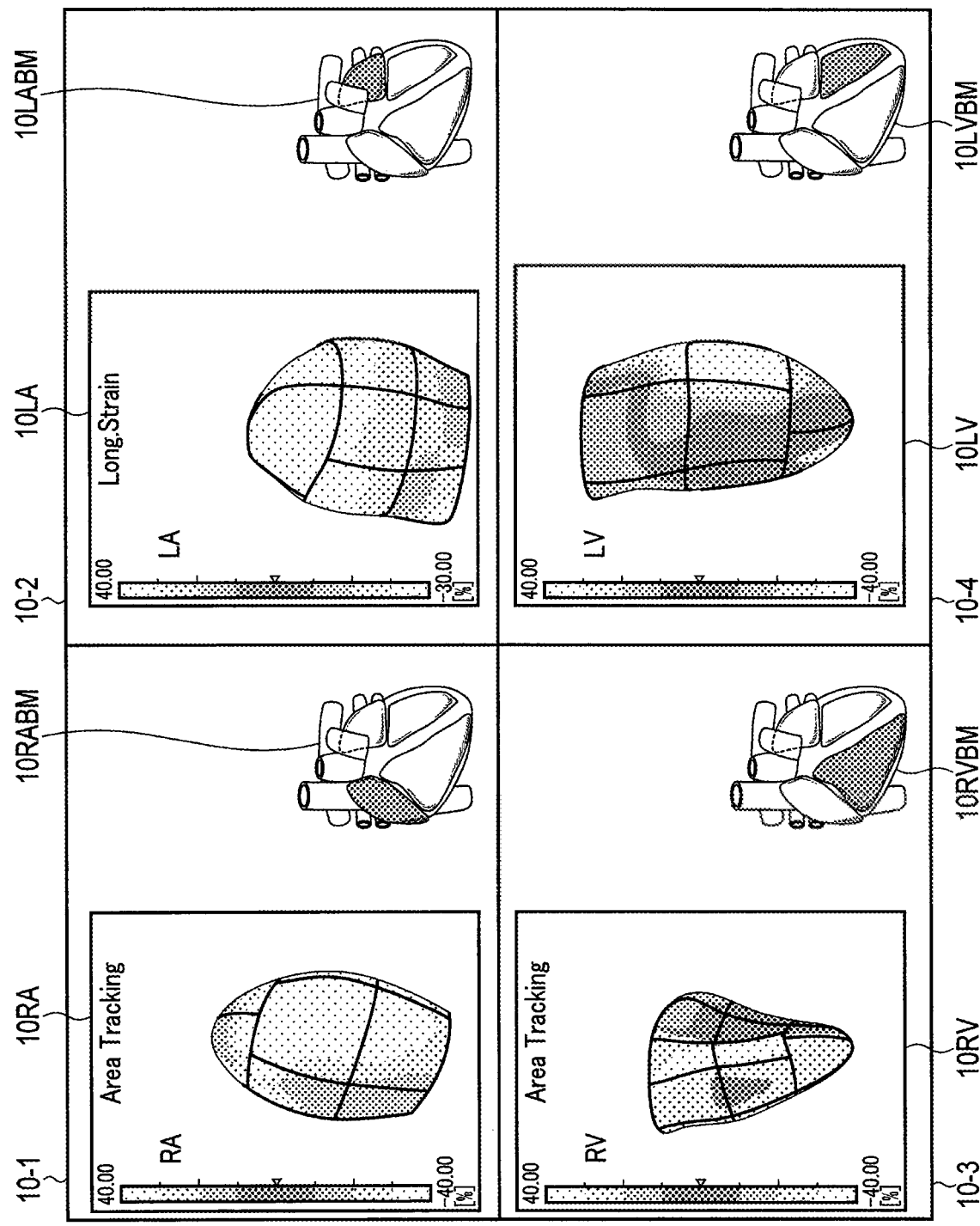
FIG. 10 shows a display example of medical information (three-dimensional display) and a body mark arranged in each of a plurality of segmented areas in the second modification of the present embodiment.

FIG. 10 shows a display example of the medical information (three-dimensional display) arranged in each of a plurality of segmented areas and the body marks arranged in each of the segmented areas. The medical information in FIG. 10 includes a single analysis result for one heart chamber. The analysis results 10RA, 10LA, 10RV, and 10LV in FIG. 10 are synchronized and displayed as moving images. In FIG. 10, each of the body marks 10RABM, 10LABM, 10RVBM, and 10LVBM is arranged at an end portion on the lower left of the segmented areas; however, the arrangement is not limited thereto. The other display examples of the arrangement of the body marks will be explained later on.

In segmented area 10-1 shown in FIG. 10, the analysis result 10RA and the body mark 10RABM are displayed. The analysis result 10RA is a three-dimensional image of the right atrium (RA) to which a color phase corresponding to a value of the analysis parameter is mapped. The body mark 10RABM schematically shows the positional relationship of four chambers with respect to the entire heart when observed from the front, and shows the area corresponding to the right atrium in highlight. In segmented area 10-2 shown in FIG. 10, the analysis result 10LA and the body mark 10LABM are displayed. The analysis result 10LA is a three-dimensional image of the left atrium (LA) to which a color phase corresponding to a value of the analysis parameter is mapped. The body mark 10LABM schematically shows the positional relationship of four chambers with respect to the entire heart when observed from the front, and shows the area corresponding to the left atrium in highlight. In segmented area 10-3 shown in FIG. 10, the analysis result 10RV and the body mark 10RVBM are displayed. The analysis result 10RV is a three-dimensional image of the right ventricle (RV) to which a color phase corresponding to a value of the analysis parameter is mapped. The body mark 10RVBM schematically shows the positional relationship of four chambers with respect to the entire heart when observed from the front, and shows the area corresponding to the right ventricle in highlight. In segmented area 10-4 shown in FIG. 10, the analysis result 10LV and the body mark 10LVBM are displayed. The analysis result 10LV is a three-dimensional image of the left ventricle (LV) to which a color phase corresponding to a value of the analysis parameter is mapped. The body mark 10LVBM schematically shows the positional relationship of four chambers with respect to the entire heart when observed from the front, and shows the area corresponding to the left ventricle in highlight.

Figure 11:
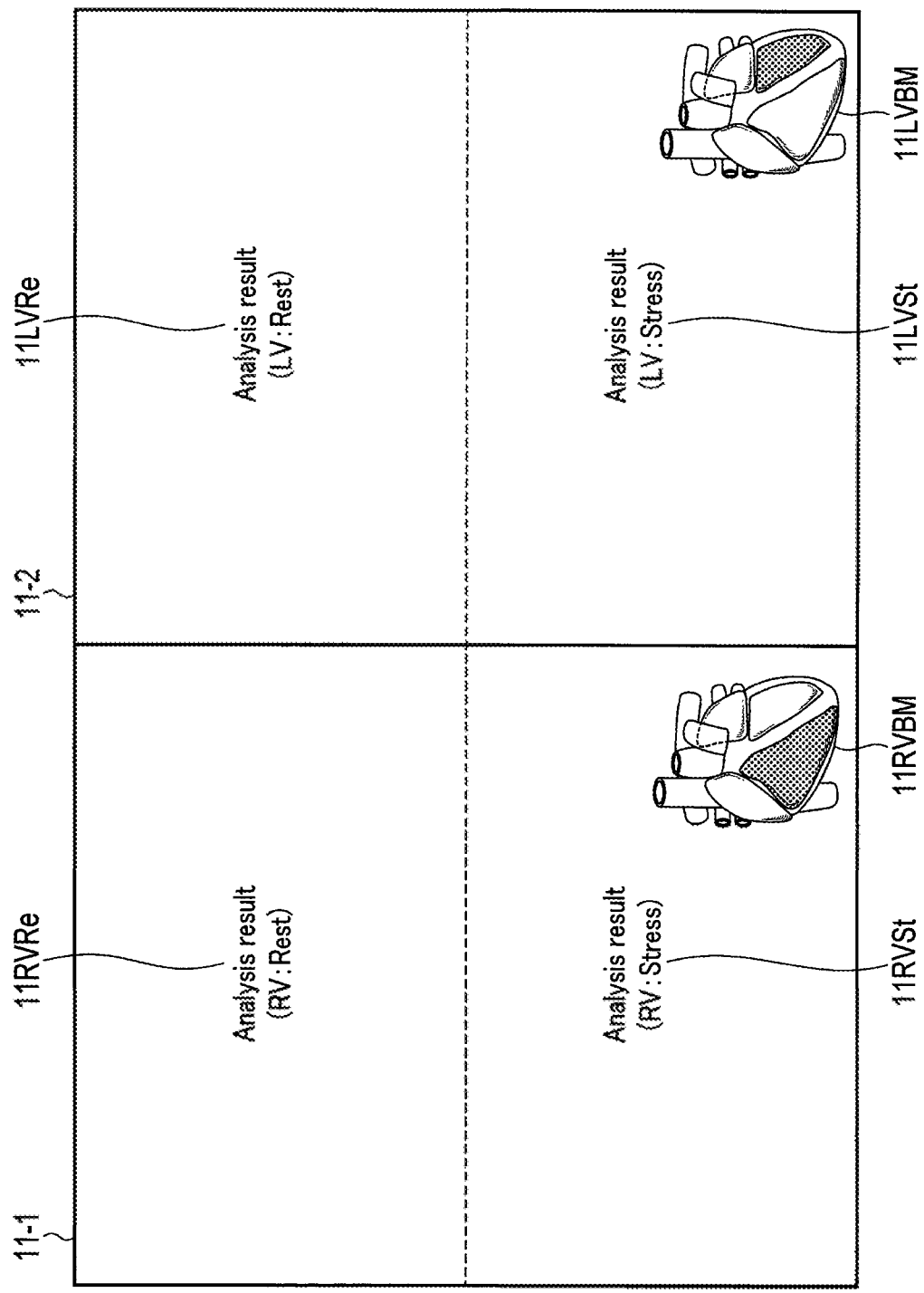
FIG. 11 shows an example of a layout of analysis results for comparing two chambers before and after stress is applied by drug infusion and an arrangement of the body mark in the second modification of the present embodiment.

FIG. 11 shows an example of a layout of the analysis results for comparing phases of the stress echo (before and after applying stress by drug infusion) and arrangement of the body mark in two heart chambers (right ventricle RV and left ventricle LV). The difference from FIG. 10 is that a plurality of analysis results are displayed for one heart chamber. The analysis results in FIG. 11 are the two types of analysis results, such as the analysis result when at rest and the analysis result under stress during the stress echo.

In segmented area 11-1 shown in FIG. 11, analysis result 11RVRe, analysis result 11RVSt, and body mark 11RVBM are arranged. The analysis result 11RVRe arranged in the upper part of the segmented area 11-1 shows the analysis result of when the right ventricle RV is at rest (RV: Rest). The analysis result 11RVSt arranged in the lower part of the segmented area 11-1 shows the analysis result of when the right ventricle RV is under stress (RV: Stress). The body mark 11RVBM schematically shows the positional relationship of four chambers with respect to the entire heart when observed from the front, and shows the area corresponding to the right ventricle in highlight. In segmented area 11-2 shown in FIG. 11, analysis result 11LVRe, analysis result 11LVSt, and body mark 11LVBM are arranged. The analysis result 11LVRe arranged in the upper part of the segmented area 11-2 shows the analysis result of when the left ventricle LV is at rest (LV: Rest). The analysis result 11LVSt arranged in the lower part of the segmented area 11-2 shows the analysis result of when the left ventricle LV is under stress (LV: Stress). The body mark 11LVBM schematically shows the positional relationship of four chambers with respect to the entire heart when observed from the front, and shows the area corresponding to the left ventricle in highlight.

Figure 12:
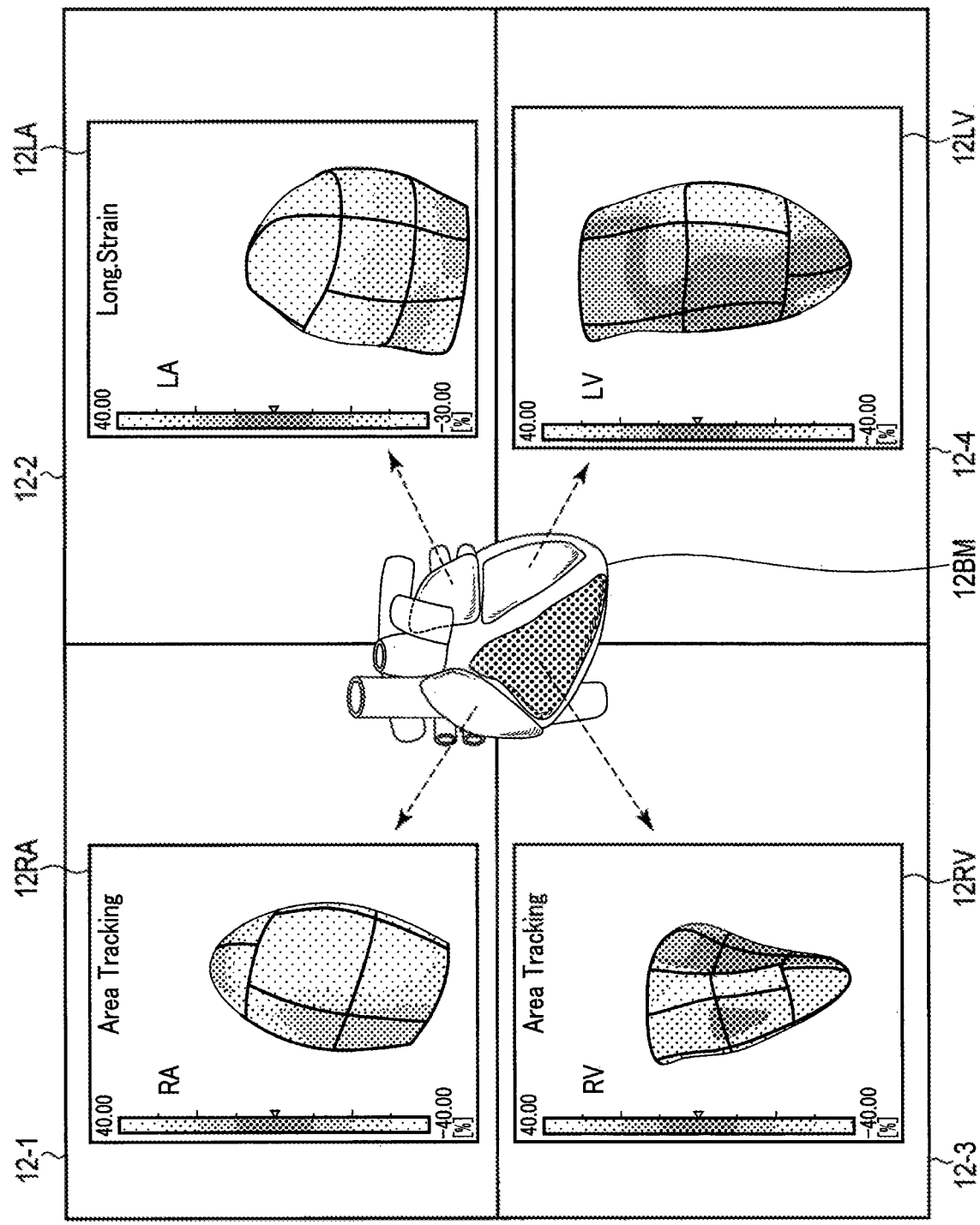
FIG. 12 shows a display example of the medical information arranged in each of the segmented areas, and the body mark arranged at the center of a display area in the second modification of the present embodiment.

FIG. 12 shows a display example of the medical information (three-dimensional display) arranged in each of a plurality of segmented areas and the body mark arranged at the center of the display area. Analysis result 12RA in segmented area 12-1, analysis result 12LA in segmented area 12-2, analysis result 12RV in segmented area 12-3, and analysis result 12LV in segmented area 12-4 in FIG. 12 correspond to the analysis results 10RA, 10LA, 10RV, and 10LV in FIG. 10. The difference between FIG. 12 and FIG. 10 lies in the display position of the body mark. Body mark 12BM in FIG. 12 is arranged at approximately the center of the display area of the display. As shown by the dotted line in FIG. 12, the orientation (posture) of the body mark 12BM corresponds to the layout (alignment) of the analysis results. In response to an input operation to the analysis result (rotation etc. of three-dimensional image), in the body mark 12BM, the display aspect of the area of the heart chamber in the analysis result concerning the input operation may be changed. The change in display aspect indicates, for example, the highlighting mentioned above. In FIG. 12, an area of the right ventricle of the body mark 12BM is highlighted by an input operation to the analysis result 12RV.

Figure 13:
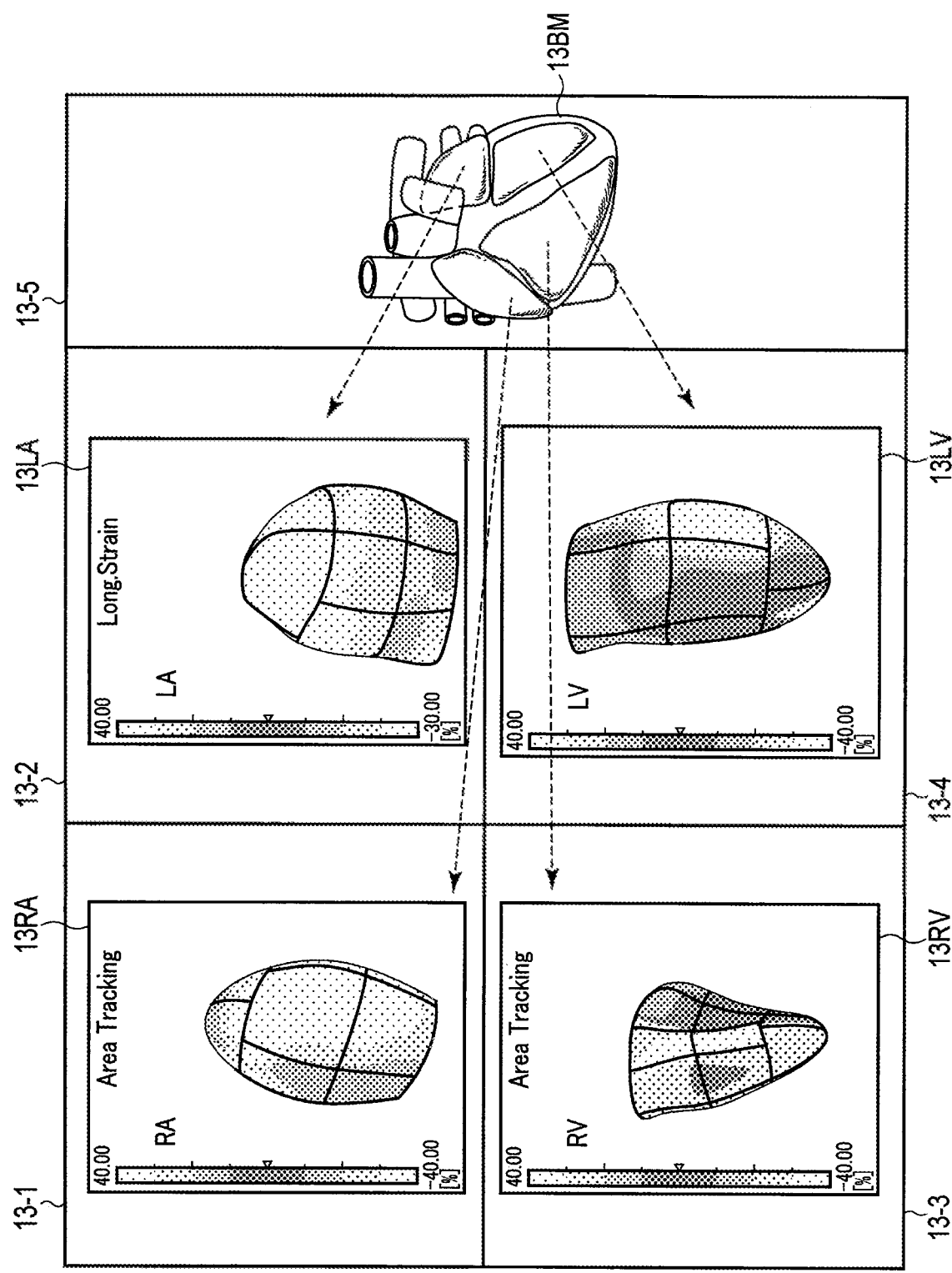
FIG. 13 shows a display example of the medical information arranged in each of the segmented areas, and the body mark arranged in an edge area of the display area in the second modification of the present embodiment.

FIG. 13 shows a display example of the medical information (three-dimensional display) arranged in each of the segmented areas and the body mark arranged at an area on the end of the display area. Analysis result 13RA in segmented area 13-1, analysis result 13LA in segmented area 13-2, analysis result 13RV in segmented area 13-3, and analysis result 13LV in segmented area 13-4 in FIG. 13 correspond to the analysis results 10RA, 10LA, 10RV, and 10LV in FIG. 10. The difference between FIG. 13 and FIG. 10 lies in the display position of the body mark. Body mark 13BM is arranged in end area 13-5 of the display area of the display. The end area is not limited to the vicinity of a corner of the display area of the display 15, and can be set at any position in the display area. As shown by the dotted line in FIG. 13, the orientation (posture) of the body mark 13BM corresponds to the layout (alignment) of the analysis results. In response to an input operation with respect to the analysis result (rotation etc. of three-dimensional image rotation), in the body mark 13BM, the display aspect of the area of the heart chamber in the analysis result concerning the input operation may be changed.

Figure 14:
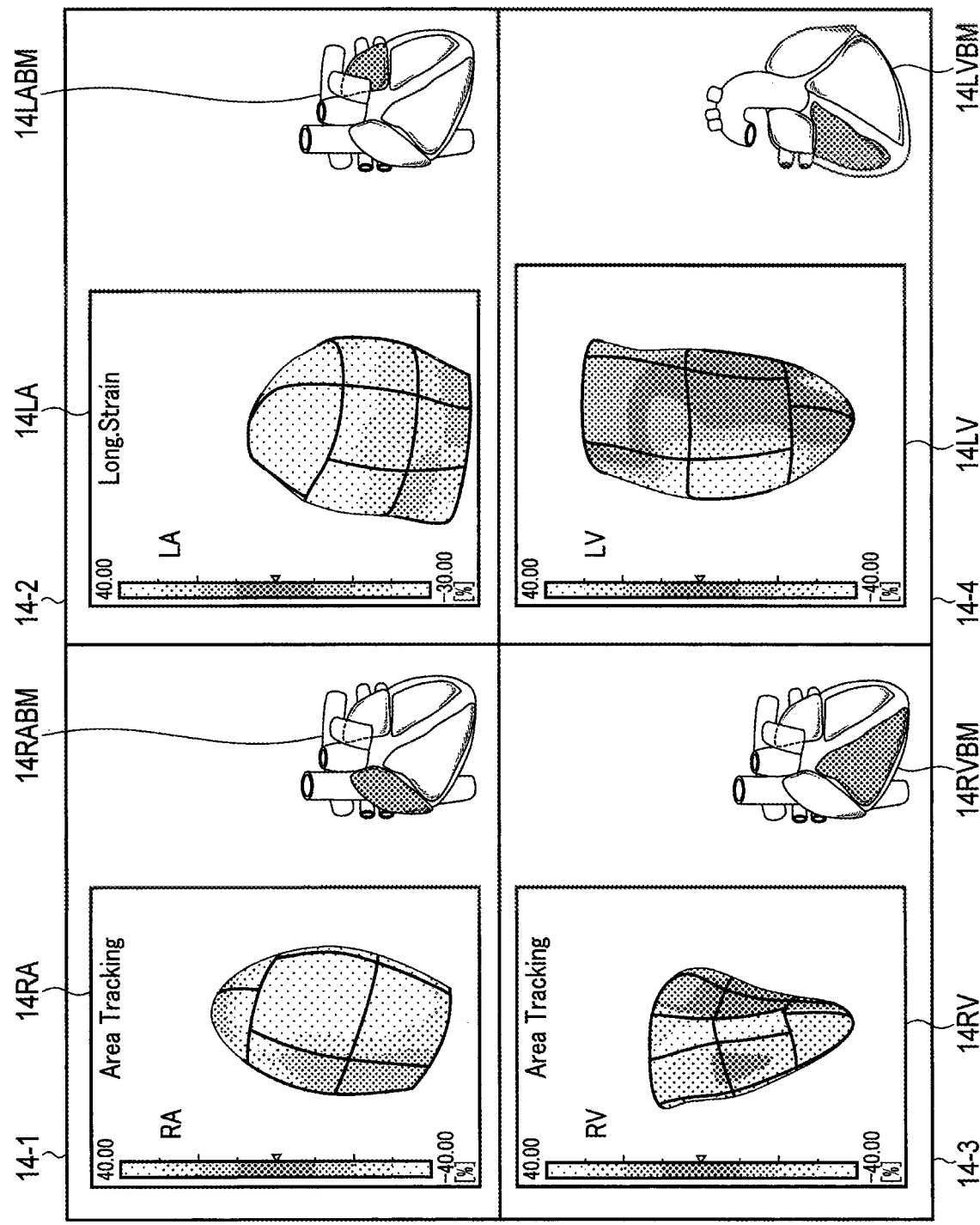
FIG. 14 shows a display example of the medical information arranged in each of the segmented areas, and the body marks arranged in each of the segmented areas in the second modification of the present embodiment.

FIG. 14 shows a display example of the medical information (three-dimensional display) arranged in each of the segmented areas and the body marks arranged in each of the segmented areas. Analysis result 14RA in segmented area 14-1, analysis result 14LA in segmented area 14-2, and analysis result 14RV in segmented area 14-3 in FIG. 14 correspond to the analysis results 10RA, 10LA, and 10RV in FIG. 10. Analysis result 14LV in segmented area 14-4 corresponds to the analysis result 8LV in FIG. 8. Body mark 14RABM in the segmented area 14-1, body mark 14LABM in the segmented area 14-2, and body mark 14RVBM in the segmented area 14-3 in FIG. 14 correspond to the body marks 10RABM, 10LABM, and 10RVBM in FIG. 10. Body mark 14LVBM in the segmented area 14-4 corresponds to the body mark 8BM in FIG. 8. The difference between FIG. 14 and FIG. 10 lies in that the analysis result 14LV and the body mark LVBM are displayed in a state of being observed from the back side of the heart. The display example of FIG. 14 is realized by executing the processing in steps Sb6 and Sb7 of the first modification in the processing in step Sc4.

Figure 15:
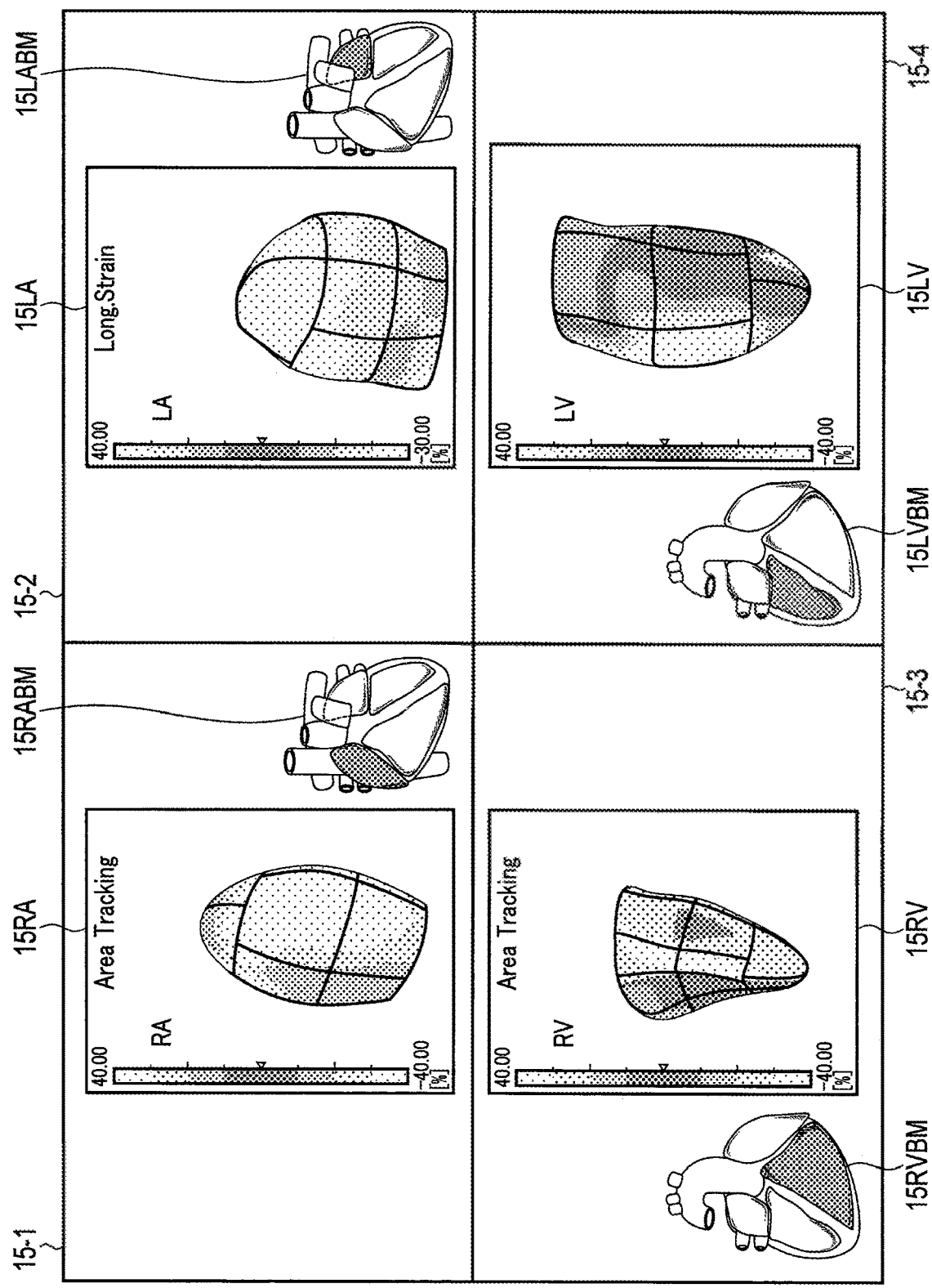
FIG. 15 shows a display example of the medical information arranged in each of the segmented areas, and the body marks arranged in each of the segmented areas in the second modification of the present embodiment.

FIG. 15 shows a display example of the medical information (three-dimensional display) arranged in each of the segmented areas and the body marks arranged in each of the segmented areas. Analysis result 15RA in segmented area 15-1, analysis result 15LA in segmented area 15-2, and analysis result 15LV in segmented area 15-4 in FIG. 15 correspond to the analysis results 14RA, 14LA, and 14LV in FIG. 14. Analysis result 15RV in segmented area 15-3 shows a state of observing a three-dimensional image of the right ventricle (RV) from the back of the subject P, to which a color phase corresponding to a value of the analysis parameter is mapped. Body mark 15RABM in the segmented area 15-1, body mark 15LABM in the segmented area 15-2, and body mark 15LVBM in the segmented area 15-4 in FIG. 15 correspond to the body marks 14RABM, 14LABM, and 14LVBM in FIG. 14. Body mark 15RVBM in segmented area 15-3 is oriented in the same manner as the three-dimensional image in the analysis result 15RV, and is displayed. The difference between FIG. 15 and FIG. 14 lies in that the analysis result 15RV and the body mark 15RVBM are displayed in a state of being observed from the back side of the heart, and the display position of the body mark in each of the segmented areas is different according to the posture of the three-dimensional image in the analysis result (front or back view). The display example of FIG. 15 is realized by executing the processing in steps Sb6 and Sb7 of the first modification in the processing in step Sc4. In addition, in the processing of step Sc6, the display position of the body mark in the segmented area is determined based on a rendering direction with respect to three-dimensional body mark data. In the display example of FIG. 15, the body mark observed from the front side of the heart is displayed on the right side of the segmented area, and the body mark observed from the back side of the heart is displayed on the left side of the segmented area.

According to the configurations mentioned above, the following effects may be obtained.

According to the ultrasound diagnostic apparatus 1 and the medical processing apparatus 20 of the present modification, an area of a structure regarding medical information can be displayed in different display aspects in a body mark in accordance with the medical information. According to the present modification, a display position of the body mark corresponding to the medical information can be determined based on a rendering direction in the rendering condition. In addition, according to the present modification, when the medical information displayed on the display 15 is selected by the operator, a body mark can be acquired in which the display aspect of the area of the structure regarding the selected medical information is different from the display aspect in the areas of the other structures. In the case where, for example, the structures are the first structure and the second structure, and the medical information is the first medical information regarding the first structure and the second medical information regarding the second structure, the first area corresponding to the first structure and the second area corresponding to the second structure can be included in the body mark, and a relative positional relationship between the first area and the second area in the body mark can be displayed by being corresponded to the alignment (layout) of the first medical information and the second medical information in the display area of the display 15. Here, in accordance with the choice of the first medical information, the body mark in which the display aspect of the area corresponding to the first structure is different from the display aspect of the area corresponding to the second structure can be displayed on the display 15.

Therefore, according to the present modification, a medical image of each of the structures can be displayed together with a body mark in which an area of the structure regarding the medical information is emphasized. For example, with respect to an analysis result of one heart chamber, one body mark in which an area corresponding to this heart chamber is highlighted can be acquired and displayed. Furthermore, with respect to a plurality of analysis results corresponding to a plurality of heart chambers, one body mark that includes these heart chambers can be acquired and displayed. In such case, the body mark can be displayed in an orientation (posture) in accordance with the layout of the analysis results. In addition, the acquired body mark can be displayed by changing the position of the body mark in the segmented area in accordance with the orientation of the three-dimensional images, that is, by changing the rendering direction, in the analysis results.

Therefore, according to the present embodiment, a body mark showing a broad view of a plurality of structures in the heart can be displayed together with medical information regarding the structures by corresponding the body mark to the orientation of a three-dimensional image in a medical image, or to a layout of the medical information. In this manner, an operator is capable of grasping the analysis results with respect to the structures in a broad view. In addition, even in a case where the heart of the subject P is deformed by a disease such as auxocardia, the operator is capable of easily ascertaining the position of the structures regarding the analysis results with respect to the entire heart. Therefore, according to the present embodiment, since the heart function analysis can be executed in a broad view, the usability of when simultaneously displaying medical information regarding the structures of a heart can be improved, which, as a result, would improve diagnostic efficiency.

Third Modification

The difference from the above embodiment is that, in the case where medical information includes a cross-sectional image showing a cross-sectional surface of a heart, a cross-section mark indicating the position of the cross-sectional surface is superimposed on a body mark (for example, a three-dimensional body mark).

The processing circuitry 37 executing the image processing function 371 generates a plurality of cross-sectional images corresponding to a plurality of cross-sectional surfaces of the heart by applying MPR processing with respect to volume data. The cross-sectional surfaces may be any cross-sectional surface with respect to the heart. For an easy-to-understand explanation, hereinafter, the cross-sectional surfaces will be explained as a reference cross-sectional surface of the heart. Here, the cross-sectional images are, for example, an apical four-chamber cross-sectional image (LV 2D 4chView), an apical left ventricle longitudinal axis cross-sectional image (LV 2D 3chView), and an apical two-chamber cross-sectional image (LV 2D 2chView). A color phase corresponding to the value of an analysis parameter may be mapped to each of the cross-sectional images.

The processing circuitry 37 that executes the display control function 377 superimposes a cross-section mark indicating a position of the reference cross-sectional surface on a body mark based on the position of the reference cross-sectional surface with respect to the volume data. The processing circuitry 37 displays the cross-sectional images together with the body mark to which at least one cross-section mark is superimposed.

Figure 16:
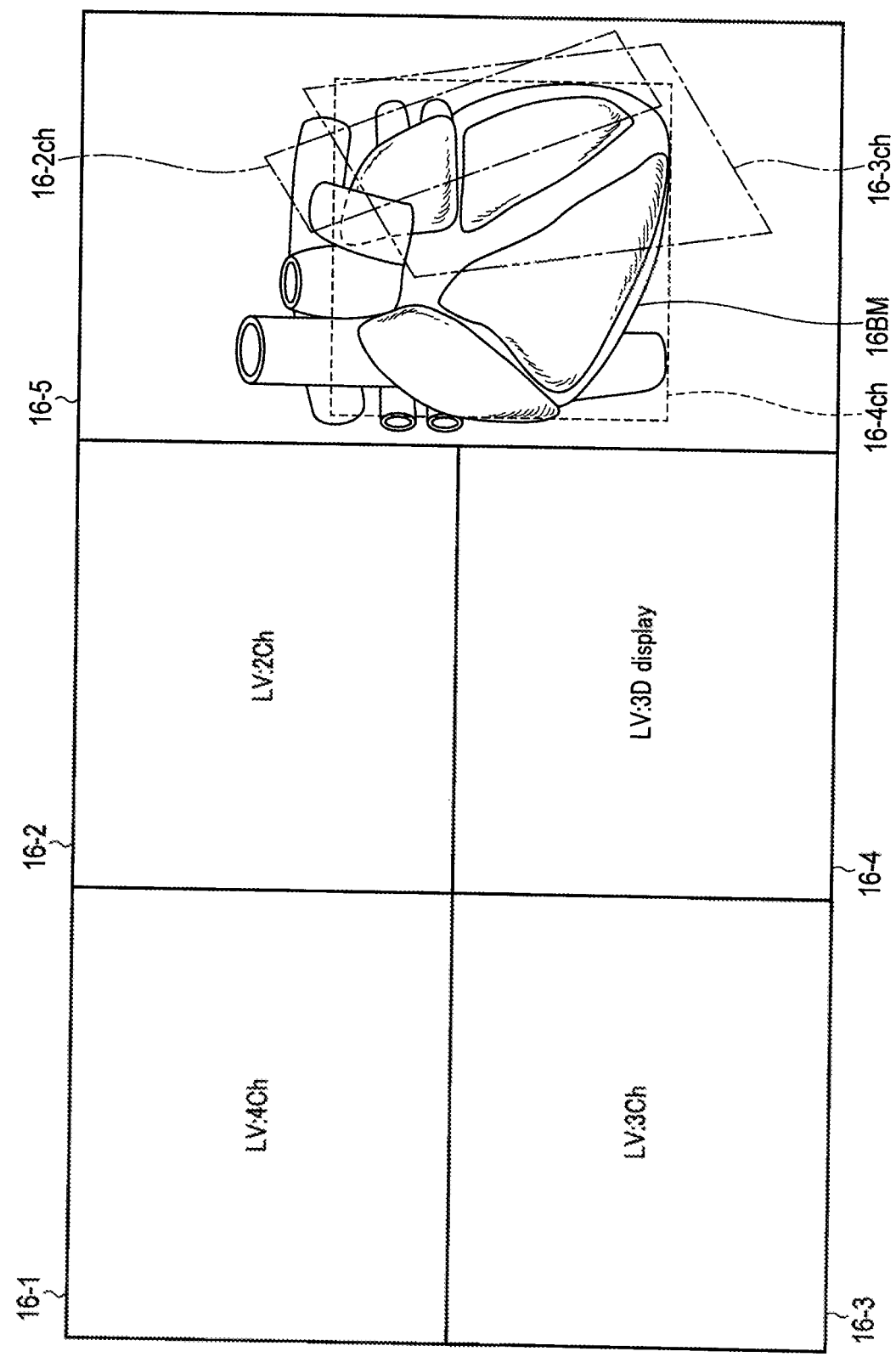
FIG. 16 shows a display example of a body mark, on which a cross-sectional surface is superimposed, together with a plurality of cross-sectional images and a three-dimensional image regarding one heart chamber in a third modification of the present embodiment.

FIG. 16 shows a display example of displaying a body mark on which a cross-section mark is superimposed together with a plurality of cross-sectional images and one three-dimensional image in one heart chamber (left ventricle LV). In FIG. 16, the apical four-chamber cross-sectional image (LV:4Ch) is displayed in segmented area 16-1, the apical two-chamber cross-sectional image (LV:2Ch) is displayed in segmented area 16-2, the apical left ventricle longitudinal axis cross-sectional image (LV:3Ch) is displayed in segmented area 16-3, a three-dimensional image of the left ventricle (LV:3D display) is displayed in segmented area 16-4, and a body mark 16BM is displayed in segmented area 16-5. In the body mark 16BM, a cross-section mark 16-4*ch* corresponding to the apical four-chamber cross-sectional image, a cross-section mark 16-2*ch* corresponding to the apical two-chamber cross-sectional image, and a cross-section mark 16-3 corresponding to the apical left ventricle longitudinal axis cross-sectional image are superimposed and are displayed.

As an application of the present modification, at least one heart chamber and at least one valve may be adopted as the structures. Here, the structures are, for example, the left ventricle, the mitral valve, and the left atrium. A color phase corresponding to the value of an analysis parameter regarding each structure may be mapped to the images regarding these structures. These images may be cross-sectional images or three-dimensional images regarding the structures.

According to the configurations mentioned above, the following effects may be obtained.

According to the ultrasound diagnostic apparatus 1 and the medical processing apparatus 20 of the present modification, in the case where the medical information includes a cross-sectional image showing a cross-sectional surface of the heart, a cross-section mark can be superimposed on the body mark and displayed. In the above manner, the present modification is capable of displaying a body mark comprehensively showing cross-sectional surfaces regarding the medical information and the structures in the heart together with medical information regarding each of the one or more structures. Therefore, since an operator is capable of comprehensively ascertaining the analysis results with respect to the structures and comprehensively executing the heart function analysis, the usability when simultaneously displaying medical information regarding the structures of a heart can be improved, which, as a result, would improve diagnostic efficiency.

Fourth Modification

The difference from the above embodiment and various modifications is that a body mark is displayed on the display 15 prior to an analysis of image data, the image data in response to a selection instruction with respect to a structure in the body mark that is displayed prior to analysis is analyzed, and an analysis result regarding the structure selected by the selection instruction is generated.

The processing circuitry 37 realizing the body mark acquisition function 375 reads data of the body mark from the storage circuitry 33 or an image storage device prior to analyzing the image data by the analysis function 373, or prior to scanning a subject P. The body mark to be read is a body mark to which the selection instruction with respect to a structure of an analysis target can be input, and is, for example, the body mark shown in FIG. 3 or FIG. 4. Here, information regarding the name of each the structures in the body mark is added to data of the body mark.

The processing circuitry 37 that realizes the display control function 377 displays the read body mark on the display 15. When the selection instruction of the structure of the analysis target is input to the body mark displayed prior to analysis by an operator through the input interface circuitry 13, the processing circuitry 37 identifies the name corresponding to the selected structure as the analysis target.

The processing circuitry 37 that realizes the analysis function 373 analyzes the image data corresponding to the identified analysis target. That is, the processing circuitry 37 analyzes the image data in response to the selection instruction with respect to the structures in the body mark displayed prior to analysis, and generates the analysis result regarding the structure selected by the selection instruction.

The above processing according to the present modification is executed, for example, in step Sa1 in FIG. 2, and in step Sb1 in FIG. 6.

According to the configurations mentioned above, the following effects may be obtained.

According to the ultrasound diagnostic apparatus 1 and the medical processing apparatus 20 of the present modification, a body mark is displayed on the display 15 prior to the analysis of image data, the image data is analyzed in response to a selection instruction with respect to a structure in the body mark that is displayed prior to analysis, and the analysis result regarding the structure selected by the selection instruction can be generated. That is, according to the present modification, a body mark can be used as a user interface for selecting a structure of an analysis target prior to executing a heart function analysis. Therefore, according to the present modification, when inputting the name of the heart chamber of the analysis target, two inputs such as an input for displaying a list of heart chamber names in a pull-down form, and an input of instruction for selecting a heart chamber name of the analysis target from the displayed list of heart chamber names can be consolidated into one operation such as the selection instruction of the structure in the body mark. Therefore, when performing input regarding the analysis target in the heart function analysis, usability is improved, which would improve diagnostic efficiency.

Fifth Modification

The difference from the above embodiment and various modifications is that, in the case where a structure that is different from a structure regarding an analysis result is selected in a body mark that is displayed on the display 15 together with the analysis result, an analysis result regarding the different structure is displayed on the display 15 together with the body mark. The body mark according to the present modification is a body mark to which a selection instruction with respect to the structure in the body mark can be input. Here, information regarding the name of each of the structures is added to the data of the body mark.

In the structures in the body mark displayed together with the analysis result on the display 15, the input interface circuitry 13 selects a structure that is different from the structure regarding the analysis result displayed on the display 15 by the instruction of an operator.

The processing circuitry 37 realizing the display control function 377 displays on the display 15 the analysis result regarding the different structure that has been selected together with the body mark. Specifically, the processing circuitry 37 identifies the name of the structure corresponding to the selected structure. The processing circuitry 37 uses the identified name to read the analysis result of the selected structure from the storage circuitry 33. The processing circuitry 37 displays the read analysis result on the display 15 together with the body mark.

The above processing according to the present modification can be executed, for example, after the processing of step Sa5 in FIG. 2, after the processing of step Sb8 in FIG. 6, and after the processing of step Sc8 in FIG. 6, respectively. When, for example, a selection instruction is input with respect to the position of the right ventricle in the body marks shown in FIG. 5, FIG. 8, FIG. 11, and FIG. 16, an analysis result regarding the right ventricle is displayed on the display 15 together with the body mark.

As an application with respect to the present modification, in the case where a structure regarding an analysis result is designated in the body mark displayed on the display 15 together with the analysis result, the image data regarding the designated structure may be reanalyzed, and the analysis result generated by reanalyzing the image data may be displayed on the display 15 together with the body mark.

Specifically, by the instruction of an operator, the input interface circuitry 13 designates a structure regarding the analysis result in the body mark displayed on the display 15 together with the analysis result. The processing circuitry 37 that realizes the analysis function 373 reanalyzes the image data regarding the designated structure. The processing circuitry 37, for example, re-executes a wall motion analysis with respect to volume data of each of the heart chambers by resetting an initial outline, etc. The processing circuitry 37 realizing the display control function 377 displays the analysis result generated by reanalyzing the image data on the display 15 together with the body mark.

According to the configurations mentioned above, the following effects may be obtained.

According to the ultrasound diagnostic apparatus 1 and the medical processing apparatus 20 of the present modification, in the case where a structure that is different from the structure regarding the analysis result is selected in the body mark displayed together with the analysis result on the display 15, the analysis result regarding the different structure is displayed on the display 15 together with the body mark. That is, according to the present modification, the body mark displayed on the display 15 together with the analysis result can be used as a user interface for displaying the analysis result of the different structure.

Furthermore, according to an application of the present modification, in the case where a structure regarding an analysis result is designated in the body mark displayed together with the analysis result on the display 15, the image data regarding the designated structure is reanalyzed, and the analysis result generated by reanalyzing the image data can be displayed on the display 15 together with the body mark. That is, according to the application of the present modification, the body mark displayed on the display 15 together with the analysis result can be used as a user interface for executing reanalysis.

Therefore, according to the present modification, by using the body mark as the user interface, a structure regarding display switching of analysis results can be comprehensively selected. This would improve usability and diagnostic efficiency since the structure concerning the execution of reanalysis can be designated in a broad view.

Furthermore, as a modification of the present embodiment, in the case of realizing the configuration of the present ultrasound diagnostic apparatus 1 by the medical processing apparatus 20, the processing of step Sa2 in the flowchart shown in FIG. 2 would be "read medical image in a time series from storage circuitry 33 or image storage device." Furthermore, the processing of step Sb2 in the flowchart shown in FIG. 6 would be "read volume data in a time series including heart chamber of analysis target from storage circuitry 33 or image storage device." In addition, the processing of step Sc1 in the flowchart shown in FIG. 9 would be "read time series image data including a plurality of heart chambers from storage circuitry 33 or image storage device." The above-mentioned image data and volume data, etc. may also be an image collected by other modalities such as an X-ray computed tomography apparatus or a magnetic resonance imaging apparatus. In addition, the analysis result may also be an analysis result performed by other modalities, etc.

In addition, the image processing function 371, the analysis function 373, the body mark acquisition function 375, and the display control function 377 of the present embodiment can also be realized by installing a program (medical processing program) that executes these functions in a computer, such as a work station, and expanding these functions in a memory. Here, the medical processing program causes the computer to acquire a body mark schematically showing at least one of a positional relationship of the structures in the heart and a position of the structure with respect to the entire heart, and to display the body mark on a display together with medical information of each of the structures based on the scanning result with respect to the subject P. By executing the medical processing program, a medical processing method can be realized that acquires a body mark schematically showing the positional relationship of the structures in the heart, analyzes image data acquired by scanning a subject P where at least two structures in the heart of the subject P are considered as analysis targets, and displays the acquired body mark on a display together with the analysis results of at least two structures. The program that causes a computer to execute the above method can be stored and distributed on various types of portable storage media such as a magnetic disc, an optical disc, or a semiconductor memory.

According to the ultrasound diagnostic apparatus 1 and the medical processing apparatus 20 of the embodiment and at least one of the modifications, etc. mentioned above, medical information of a structure of a heart can be comprehensively shown, which would allow usability to improve when simultaneously displaying the medical information concerning the structures of the heart.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. A medical processing apparatus comprising processing circuitry configured to:
   obtain an image that shows a positional relation of at least two structures selected from among a left ventricle, a left atrium, a right ventricle, and a right atrium in a heart of a subject,
   analyze acquired image data as analysis targets which are the at least two structures in the heart of the subject, the acquired image data being acquired by scanning the subject,
   generate analysis results for each of the at least two structures, and
   display the image on a display together with the analysis results, wherein
   the processing circuitry is configured to display the image and the analysis results on the display as moving images in accordance with a heart time phase,
   the image includes a three-dimensional schematic image,
   the analysis results, for each of the at least two structures, includes a three-dimensional analysis image and a polar map image,
   a rendering direction of the three-dimensional schematic image corresponds to a rendering direction of the three-dimensional analysis image,
   when the analysis results corresponding to a first structure of the at least one of the two structures are displayed, a part of the three-dimensional schematic image corresponding to the first structure is emphasized, and
   when the analysis results corresponding to a second structure of the at least one of the two structures are displayed, a part of the three-dimensional schematic image corresponding to the second structure is emphasized.

2. The medical processing apparatus according to claim 1, wherein the processing circuitry is configured to display the analysis results of each of the at least two structures in respective individual display areas on the display.

3. The medical processing apparatus according to claim 2, wherein
   the at least two structures include the first structure and the second structure,
   the image includes a first area corresponding to the first structure and a second area corresponding to the second structure, and
   a relative positional relationship between the first area and the second area in the image displayed on the display corresponds to an arrangement of the analysis results corresponding to the first structure and the analysis results corresponding to the second structure displayed on the display.

4. The medical processing apparatus according to claim 1, wherein
   the at least two structures include a structure other than an analysis target, and
   in the image, a display aspect of an area corresponding to the analysis target is different from a display aspect of an area corresponding to the structure other than the analysis target.

5. The medical processing apparatus according to claim 1, wherein the three-dimensional schematic image shows a three-dimensional positional relationship of the at least two structures.

6. The medical processing apparatus according to claim 5, wherein the processing circuitry is configured to
   generate rendering images of volume data that is acquired as the analysis results corresponding to the first structure and the analysis results corresponding to the second structure, and
   acquire the three-dimensional image in accordance with a rendering condition used for generating the rendering images.

7. The medical processing apparatus according to claim 6, wherein the processing circuitry is configured to
   execute registration between the volume data and the three-dimensional image, and
   acquire the three-dimensional image by rendering the three-dimensional image after the registration in accordance with a condition corresponding to the rendering condition.

8. The medical processing apparatus according to claim 5, wherein the three-dimensional image includes a cross-section mark indicating a position of a reference cross-sectional surface of the heart.

9. The medical processing apparatus according to claim 1, wherein the processing circuitry is configured to
   display the image on the display prior to analyzing the acquired image data,
   analyze the acquired image data in response to a selection instruction with respect to the at least two structures in the image displayed prior to the analyzing the acquired image data, and
   generate the analysis results corresponding to the first structure and the analysis results corresponding to the second structure based on the selection instruction.

10. The medical processing apparatus according to claim 1, wherein, in response to a structure that is different from a structure included in the analysis results corresponding to the first structure and the analysis results corresponding to the second structure being selected in the image displayed together with the analysis results corresponding to the first structure and the analysis results corresponding to the second structure on the display, the processing circuitry is configured to display analysis results corresponding to the different structure on the display together with the image.

11. The medical processing apparatus according to claim 1, wherein, in response to a structure included in the analysis results corresponding to the first structure and the analysis results corresponding to the second structure being designated in the image displayed on the display together with the analysis results corresponding to the first structure and the analysis results corresponding to the second structure, the processing circuitry is configured to reanalyze the acquired image data regarding the designated structure, and to display analysis results generated by reanalyzing the acquired image data on the display together with the image.

12. An ultrasound diagnostic apparatus comprising the medical processing apparatus according to claim 1.

13. The medical processing apparatus according to claim 1, wherein the processing circuitry is configured to:
   display a two-dimensional cross-sectional image of the heart obtained based on the acquired image data on the display, and
   display the image, the analysis results corresponding to the first structure and the analysis results corresponding to the second structure, and the two-dimensional cross-sectional image on the display together as the moving images in accordance with the heart time phase.

14. The medical processing apparatus according to claim 1, wherein the processing circuitry is configured to display a two-dimensional cross-sectional image of the heart obtained based on the acquired image data on the display with the image in accordance with the heart time phase.

15. The medical processing apparatus according to claim 14, wherein the processing circuitry is configured to display an object indicating a position of the two-dimensional cross-sectional image in the image on the display together with the image.

16. The medical processing apparatus according to claim 1, wherein the processing circuitry is configured to:
   display on the display a plurality of two-dimensional cross-sectional images showing different cross-sectional surfaces of the heart obtained based on the acquired image data,
   display the image and the plurality of two-dimensional cross-sectional images on the display as moving images in accordance with a heart time phase, and
   display a plurality of objects indicating positions of the plurality of two-dimensional cross-sectional images in the image on the display together with the image.

17. The medical processing apparatus according to claim 1, wherein the image shows shapes of the at least two structures.

18. The medical processing apparatus according to claim 17, wherein
   the acquired image data is volume data obtained by scanning the heart, and
   the image is generated based on the volume data.

19. The medical processing apparatus according to claim 1, wherein each of the image, the analysis results corresponding to the first structure, and the analysis results corresponding to the second structure includes a surface rendering image or a volume rendering image.

20. A medical processing method comprising:
   obtaining an image that shows a positional relation of at least two structures selected from among a left ventricle, a left atrium, a right ventricle, and a right atrium in a heart of a subject,
   analyzing acquired image data as analysis targets which are the at least two structures in the heart of the subject, the acquired image data being acquired by scanning the subject,
   generating analysis results for each of the at least two structures, and
   displaying the image on a display together with the analysis results, wherein
   the method further comprises displaying the image and the analysis results on the display as moving images in accordance with a heart time phase,
   the image includes a three-dimensional schematic image,
   the analysis results, for each of the at least two structures, includes a three-dimensional analysis image and a polar map image,
   a rendering direction of the three-dimensional schematic image corresponds to a rendering direction of the three-dimensional analysis image,
   when the analysis results corresponding to a first structure of the at least one of the two structures are displayed, a part of the three-dimensional schematic image corresponding to the first structure is emphasized, and
   when the analysis results corresponding to a second structure of the at least one of the two structures are displayed, a part of the three-dimensional schematic image corresponding to the second structure is emphasized.

21. A medical processing apparatus comprising processing circuitry configured to
   obtain an image, which is a three-dimensional image showing a positional relation and shapes of structures of a left ventricle, a left atrium, a right ventricle, and a right atrium in a heart of a subject,
   generate analysis results by analyzing, with the left ventricle and the left atrium in the heart of the subject as analysis targets, acquired image data acquired by scanning the subject,
   display a plurality of two-dimensional cross-sectional images showing different cross-sectional surfaces of the heart, which are obtained based on the three-dimensional image and the acquired image data, on a display as moving images in accordance with a heart time phase, together with the analysis results of structures of the left ventricle and the left atrium, and further display a plurality of objects indicating positions of the plurality of two-dimensional cross-sectional images in the image together with the image, wherein
the image includes a three-dimensional schematic image,
the analysis results, for each of the left ventricle and the left atrium, includes a three-dimensional analysis image and a polar map image,
a rendering direction of the three-dimensional schematic image corresponds to a rendering direction of the three-dimensional analysis image,
when the analysis results corresponding to the left ventricle are displayed, a part of the three-dimensional schematic image corresponding to the left ventricle is emphasized, and
when the analysis results corresponding to the left atrium are displayed, a part of the three-dimensional schematic image corresponding to the left atrium is emphasized.

22. The medical processing apparatus according to claim 21, wherein
the acquired image data is volume data obtained by scanning the heart, and
the image is generated based on the volume data.

23. A non-transitory computer-readable storage medium storing a program to cause a computer to perform a method comprising:
obtaining an image that schematically shows a positional relation of at least two structures selected from among a left ventricle, a left atrium, a right ventricle, and a right atrium in a heart of a subject,
analyzing acquired image data as analysis targets which are the at least two structures in the heart of the subject, the acquired image data being acquired by scanning the subject,
generating analysis results for each of the at least two structures, and
displaying the image on a display together with the analysis results, wherein
the method further comprises displaying the image and the analysis results on the display as moving images in accordance with a heart time phase,
the image includes a three-dimensional schematic image,
the analysis results, for each of the at least two structures, includes a three-dimensional analysis image and a polar map image,
a rendering direction of the three-dimensional schematic image corresponds to a rendering direction of the three-dimensional analysis image,
when the analysis results corresponding to a first structure of the at least one of the two structures are displayed, a part of the three-dimensional schematic image corresponding to the first structure is emphasized, and
when the analysis results corresponding to a second structure of the at least one of the two structures are displayed, a part of the three-dimensional schematic image corresponding to the second structure is emphasized.

24. A medical processing apparatus comprising processing circuitry configured to:
acquire an image that shows a positional relation of at least two structures selected from among a left ventricle, a left atrium, a right ventricle, and a right atrium in a heart of a subject,
analyze image data of the image as analysis targets which are the at least two structures in the heart of the subject, the image data being acquired by scanning the subject,
generate analysis results for each of the at least two structures, and
display the image on a display together with the analysis results, wherein
the processing circuitry is configured to display the image and the analysis results on the display as moving images in accordance with a heart time phase,
the image includes a three-dimensional schematic image,
the analysis results, for each of the at least two structures, includes a three-dimensional analysis image and a polar map image,
a rendering direction of the three-dimensional schematic image corresponds to a rendering direction of the three-dimensional analysis image,
when the analysis results corresponding to a first structure of the at least one of the two structures are displayed, a part of the three-dimensional schematic image corresponding to the first structure is emphasized, and
when the analysis results corresponding to a second structure of the at least one of the two structures are displayed, a part of the three-dimensional schematic image corresponding to the second structure is emphasized.

25. A medical processing method comprising:
acquiring an image that shows a positional relation of at least two structures selected from among a left ventricle, a left atrium, a right ventricle, and a right atrium in a heart of a subject,
analyzing image data of the image as analysis targets which are the at least two structures in the heart of the subject, the image data being acquired by scanning the subject,
generating analysis results for each of the at least two structures, and
displaying the image on a display together with the analysis results, wherein
the method further comprises displaying the image and the analysis results on the display as moving images in accordance with a heart time phase,
the image includes a three-dimensional schematic image,
the analysis results, for each of the at least two structures, includes a three-dimensional analysis image and a polar map image,
a rendering direction of the three-dimensional schematic image corresponds to a rendering direction of the three-dimensional analysis image,
when the analysis results corresponding to a first structure of the at least one of the two structures are displayed, a part of the three-dimensional schematic image corresponding to the first structure is emphasized, and
when the analysis results corresponding to a second structure of the at least one of the two structures are displayed, a part of the three-dimensional schematic image corresponding to the second structure is emphasized.

26. A medical processing apparatus comprising processing circuitry configured to
acquire an image, which is a three-dimensional image showing a positional relation and shapes of structures of a left ventricle, a left atrium, a right ventricle, and a right atrium in a heart of a subject,
generate analysis results by analyzing, with the left ventricle and the left atrium in the heart of the subject as analysis targets, image data of the image acquired by scanning the subject,
display a plurality of two-dimensional cross-sectional images showing different cross-sectional surfaces of the heart, which are obtained based on the three-dimensional image and the image data, on a display as moving images in accordance with a heart time phase, together with the analysis results of structures of the left ventricle and the left atrium, and further display a plurality of objects indicating positions of the plurality of two-dimensional cross-sectional images in the image together with the image, wherein the image includes a three-dimensional schematic image, the analysis results, for each of the left ventricle and the left atrium, includes a three-dimensional analysis image and a polar map image, a rendering direction of the three-dimensional schematic image corresponds to a rendering direction of the three-dimensional analysis image, when the analysis results corresponding to the left ventricle are displayed, a part of the three-dimensional schematic image corresponding to the left ventricle is emphasized, and when the analysis results corresponding to the left atrium are displayed, a part of the three-dimensional schematic image corresponding to the left atrium is emphasized.

27. A non-transitory computer-readable storage medium storing a program to cause a computer to perform a method comprising:

acquiring an image that schematically shows a positional relation of at least two structures selected from among a left ventricle, a left atrium, a right ventricle, and a right atrium in a heart of a subject, analyzing image data of the image as analysis targets which are the at least two structures in the heart of the subject, the image data being acquired by scanning the subject, generating analysis results for each of the at least two structures, and displaying the image on a display together with the analysis results, wherein the method further comprises displaying the image and the analysis results on the display as moving images in accordance with a heart time phase, the image includes a three-dimensional schematic image, the analysis results, for each of the at least two structures, includes a three-dimensional analysis image and a polar map image, a rendering direction of the three-dimensional schematic image corresponds to a rendering direction of the three-dimensional analysis image, when the analysis results corresponding to a first structure of the at least one of the two structures are displayed, a part of the three-dimensional schematic image corresponding to the first structure is emphasized, and when the analysis results corresponding to a second structure of the at least one of the two structures are displayed, a part of the three-dimensional schematic image corresponding to the second structure is emphasized.

* * * * *